US009962540B2

United States Patent
Picaud et al.

(10) Patent No.: US 9,962,540 B2
(45) Date of Patent: May 8, 2018

(54) BIOCOMPATIBLE CARBON BASED ELECTRODE AND ITS PREPARATION PROCESS

(71) Applicants: UNIVERSITE PIERRE ET MARIE CURIE (PARIS 6), Paris (FR); CENTRE NATIONAL DE LA RECHERCHE SCIENTIFIQUE, Paris (FR); COMMISSARIAT A L'ENERGIE ATOMIQUE ET AUX ENERGIES ALTERNATIVES, Paris (FR)

(72) Inventors: Serge Picaud, Avon (FR); Amel Bendali, Courbevoie (FR); Philippe Bergonzo, Massy (FR); Valerie Forster-Fradot, Paris (FR); Jose-Alain Sahel, Paris (FR)

(73) Assignees: UNIVERSITE PIERRE ET MARIE CURIE (PARIS 6), Paris (FR); CENTRE NATIONAL DE LA RECHERCHE SCIENTIFIQUE, Paris (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 370 days.

(21) Appl. No.: 14/655,021

(22) PCT Filed: Dec. 24, 2013

(86) PCT No.: PCT/EP2013/077990
§ 371 (c)(1),
(2) Date: Jun. 23, 2015

(87) PCT Pub. No.: WO2014/102281
PCT Pub. Date: Jul. 3, 2014

(65) Prior Publication Data
US 2015/0343202 A1    Dec. 3, 2015

(30) Foreign Application Priority Data

Dec. 24, 2012  (EP) ..................... 12306667

(51) Int. Cl.
*A61N 1/05* (2006.01)
*A61N 1/36* (2006.01)
*B82Y 5/00* (2011.01)

(52) U.S. Cl.
CPC ............. *A61N 1/0526* (2013.01); *A61N 1/05* (2013.01); *A61N 1/0543* (2013.01);
(Continued)

(58) Field of Classification Search
CPC ... A61N 1/0526; A61N 1/0529; A61N 1/0534
(Continued)

(56) References Cited

U.S. PATENT DOCUMENTS 6,670,179 B1   12/2003  Mattson et al.
7,162,308 B2 *  1/2007  O'Brien ................. A61N 1/05
                                                     607/116

(Continued)

FOREIGN PATENT DOCUMENTS

WO    20110154455 A1    12/2011
WO    2012/162743 A1    12/2012
WO    2013/057218 A1     4/2013

OTHER PUBLICATIONS

Thalhammer et al. "The use of nanodiamond monolayer coatings to promote the formation of functional neuronal network" Biomaterials, vol. 31, No. 8, Mar. 2010. pp. 2097-2104.*
(Continued)

*Primary Examiner* — Cachet I Sellman
(74) *Attorney, Agent, or Firm* — Young & Thompson

(57) ABSTRACT

A biocompatible carbon based electrode, and its preparation process are described. The electrode is formed by first and (Continued)

second biocompatible chemically oxygen terminated or H-terminated carbon-based materials. The first material is configured to promote the growth or at least the direct interfacing of adult neurons on the first material without substantially promoting the growth and direct interfacing of glial cells on the first material. The second material presents a peptide coating to promote the growth and at least the direct interfacing of adult glial cells.

20 Claims, 23 Drawing Sheets

(52) U.S. Cl.
CPC .......... *A61N 1/0551* (2013.01); *A61N 1/0541* (2013.01); *A61N 1/36007* (2013.01); *A61N 1/36032* (2013.01); *A61N 1/36046* (2013.01); *B82Y 5/00* (2013.01)

(58) Field of Classification Search
USPC ........................................................ 607/116
See application file for complete search history.

(56) References Cited

U.S. PATENT DOCUMENTS

| 7,676,274 | B2* | 3/2010 | Hung .................. A61N 1/0526 607/116 |
| 2002/0120296 | A1 | 8/2002 | Mech et al. |
| 2003/0100823 | A1* | 5/2003 | Kipke ................ A61B 5/04001 600/378 |
| 2004/0219184 | A1 | 11/2004 | Brown et al. |
| 2011/0108433 | A1 | 5/2011 | De Sanoit et al. |
| 2011/0184269 | A1 | 7/2011 | Sauter-Starace et al. |
| 2011/0282421 | A1* | 11/2011 | Sung ................... C12N 5/0619 607/118 |
| 2013/0228547 | A1 | 9/2013 | Scorsone et al. |

OTHER PUBLICATIONS

Spect et al. "Ordered Growth of neurons on diamond." Biomaterials, vol. 25, No. 18. Aug. 2004. pp. 4073-4078.*
Polikov et al. "Response of brain tissue to chronically implanted neural electrodes" Journal of Neuroscience Methods 148 (2005) 1-18.*
Maynard et al. A technique to prevent dural adhesions to chemically implanted microelectrode arrays. Journal of Neuroscience Methods. vol. 97 No. 2. Apr. 2000. pp. 93-101.*
Bonnauron M et al.: "High aspect ratio diamond microelectrode array for neuronal activity measurements", Diamond and Related Materials, Elsevier Science Publishers, Amsterdam, NL, vol. 17, No. 7-10, Jul. 1, 2008 (Jul. 1, 2008), pp. 1399-1404, XP023785166, ISSN: 0925-9635, DOI: 10.1016/J.Diamond.2007.12.065 [retrieved on Jul. 17, 2008] the whole document.
Thalhammer A et al.: "The use of nanodiamond monolayer coatings to promote the formation of functional neuronal networks", Biomaterials, Elsevier Science Publishers BV., Barking, GB, vol. 31, No. 8, Mar. 1, 2010 (Mar. 1, 2010), pp. 2097-2104, XP026870579, ISSN: 0142-9612 [retrieved on Jan. 22, 2010] Items I, 3.1-3.3, 4.1-4.3; figure 1.
Specht C G et al.: "Ordered growth of neurons on diamond", Biomaterials, Elsevier Science Publishers BV., Barking, GB, vol . 25, No. 18, Aug. 1, 2004 (Aug. 1, 2004), pp. 4073-4078, XP004497069, ISSN: 0142-9612, DOI: 10.1016/J.Biomaterials. 2003.11.006 Items 1, 2.1,3.1,4.
Lucas H. Hess et al.: "Graphene Transistor Arrays for Recording Action Potentials from Electrogenic Cells", Advanced Materials, vol. 23, No. 43, Nov. 16, 2011 (Nov. 16, 2011), pp. 5045-5049, XP055067425, ISSN: 0935-9648, DOI: 10.1002/adma.201102990 cited in the application the whole document.
Edwin M Maynard et al.: "A technique to prevent dural adhesions to chronically implanted microelectrode arrays", Journal of Neuroscience Methods, vol. 97, No. 2, Apr. 1, 2000 (Apr. 1, 2000), pp. 93-101, XP055067413, ISSN: 0165-0270, DOI: 10.1016/S0165-0270(00)00159-X cited in the application abstract.
Tzahi Cohen-Karni et al.: "Graphene and Nanowire Transistors for Cellular Interfaces and Electrical Recording", Nano Letters, vol. 10, No. 3, Mar. 10, 2010 (Mar. 10, 2010), pp. 1098-1102, XP055067426, ISSN: 1530-6984, DOI: 10.1021/nl1002608 cited in the application abstract.
Liu Feng-Bin et al.: "Electronic properties of hydrogen- and oxygen-terminated diamond surfaces exposed to the air", Chinese Physics B, Chinese Physics B, vol. 18, No. 5, May 1, 2009 (May 1, 2009), pp. 2041-2047, XP020155373, ISSN: 1674-1056, DOI: 10.1088/1674-1056/18/5/052, Abstract.
International Search Report, dated May 8, 2014, from corresponding PCT application.
EP Search Report, dated Jun. 24, 2013, from corresponding EP application.

* cited by examiner

BIOCOMPATIBLE CARBON BASED ELECTRODE AND ITS PREPARATION PROCESS

The present invention relates to new biocompatible carbon based electrode, its use and preparation process.

Neuroprostheses and brain-machine interfaces have witnessed an exponential development since the success of cochlear implants and of deep brain stimulation for Parkinsonian patients (Lebedev and Nicolelis, 2006). Neuroprostheses can either be surface electrodes, meaning the electrodes are simply in contact to the glial surface of the neuronal tissue such as the cortex, or penetrating electrodes reaching deeper neuronal structures in the brain. Although cortical implants have shown a gain of function after a few months, this was unfortunately frequently followed by a complete loss of activity (Dobelle et al., 1974). This loss of functionality could be attributed to a major gliosis occurring around the prostheses or its electrodes in the months following implantation (Maynard et al., 2000). Another challenge for neuroprostheses is to increase the resolution of individual electrodes to stimulate more precisely discrete neuronal areas. These objectives motivate the development for new biocompatible materials limiting glial reactions and improving direct interactions with neurones.

Recently, the concept of retinal prostheses was validated in clinical trials showing that such prostheses can enable blind patients to read short words, identify contrasted objects or follow lanes on the ground (Humayun et al., 2009; Zrenner et al., 2011). These retinal prostheses aiming at restoring vision in patients having lost their photoreceptors are either placed in the subretinal space or on the epiretinal side in direct contact to either the outer or the inner limiting membrane both produced by glial Muller cells. In the first configuration, the subretinal implant will stimulate retinal bipolar cells, neurones normally postsynaptic to photoreceptors (Zrenner et al., 2011) whereas epiretinal implants are targeting retinal ganglion cells, spiking neurones sending visual information to the brain via their axon through the optic nerve (Humayun et al., 2009). Although these implants have already restored some visual functions in patients (Humayun et al., 2009; Zrenner et al., 2011), an increase in electrode resolution is required to further improve the restored visual performances to achieve face recognition, text reading or independent locomotion. Different 3D design were already proposed to reach this objective using either pillars (Butterwick et al., 2009) or wells (Djilas et al., 2011) on the implants.

Among potential new biomaterials, diamond has raised great attention for its use in neuroprostheses because Boron-doped diamond exhibits semiconductive properties. Diamond biocompatibility was already demonstrated on osteoblast cultures (Grausova L, 2009) and even embryonic cortical neurons (Specht et al., 2004; Thalhammer et al., 2010). Embryonic neurons were found to grow selectively on protein patterns stamped on diamond surfaces (Specht et al., 2004) but they could not grow directly on a polished polycrystalline diamond layer or on a nanocrystalline diamond layer unless these layers were coated with peptides or with dispersed nanodiamond particles (Thalhammer et al., 2010). The use of diamond as electrodes has further been demonstrated by recording neuronal activities using cell lines (Ariano et al., 2009).

One of the aims of the present invention is the use of new biocompatible carbon based electrodes to either promote the growth of adult neurons or increase glial cell adherence.

Another aim is to provide such new biocompatible carbon based electrodes.

Still another aim is to provide a process preparation of said electrodes.

Still another aim is the use of such electrodes for the implementation of implants or neuroprosthesis liable to prevent the gliosis.

The present invention provides therefore:

A first biocompatible chemically oxygen terminated or H-terminated carbon-based material, bound to a biocompatible second chemically oxygen terminated or H-terminated carbon-based material, said first and said second carbon-based material forming an electrode, said first material being in particular selected from the group consisting of nanocrystalline diamond which is doped by either boron, phosphorus or nitrogen, to become a semiconductor, or graphene, nanotubes, or nanotubes on diamond, the surface of which is substantially free of any peptide coating, said first carbon-based material having an electrical conductivity of at least about 0.01 S·cm$^1$, said second biocompatible chemically oxygen terminated or H-terminated carbon-based material, being identical or different from said first carbon-based material, said second carbon-based material presenting a peptide coating, in particular a peptide from the extracellular matrix, to promote the growth and at least the direct interfacing of adult glial cells, said second chemically oxygen terminated or H-terminated carbon-based material being in particular selected from the group consisting of nanocrystalline diamond which is doped in particular with boron, in particular a boron-doped hydrogen terminated diamond or oxidized diamond, graphene or nanotubes, in particular diamond grafted nanotubes, for its use to promote the growth or at least the direct interfacing of adult neurons on said material without substantially promoting the growth and direct interfacing of glial cells on said material.

An other object provided is the first biocompatible chemically oxygen terminated or H-terminated carbon-based material, bound to a biocompatible second chemically oxygen terminated or H-terminated carbon-based material, said first and said second carbon-based material forming an electrode, for its use as described above, wherein said adult neurons are found in tissues selected from the group consisting of the retina, thalamus, cortex, vestibular system, cochlea, brain stem, midbrain, colliculus, subthalamic nucleus, globus pallidus interna, zona incerta, pallidofugal fibers, periaqueductal gray, periventricular gray, internal capsule, ventral posterolateral nucleus and ventral posteromedial nucleus, subgenual cingulate gyrus, nucleus accumbens, ventral capsule/ventral striatum, inferior thalamic peduncle, lateral habenula vagus nerve, afferent nerves, spinal cord, large dorsal columns, nerves controlling muscle activity such as those for locomotion or sphincter opening.

An other object provided is the first biocompatible chemically oxygen terminated or H-terminated carbon-based material, bound to a biocompatible second chemically oxygen terminated or H-terminated carbon-based material, said first and said second carbon-based material forming an electrode, for its use as described above, wherein said electrode is shaped like a penetrating electrode, such as a penetrating needle, in particular a tri-dimensional needle, or is positioned on a penetrating support, which can be shaped like a needle, in particular a tri-dimensional needle, and in particular, a plurality of electrodes being combined to form an electrode array, and more particularly said electrode or electrode array is fixed on a support to form an implant or a prosthesis, in particular wherein the length of said penetrating needle and/or electrode is comprised from about 10 μm to about 1 to 2 cm and the diameter is comprised from 20 μm to about 500 μm.

An other object provided is the first biocompatible chemically oxygen terminated or H-terminated carbon-based material, bound to a biocompatible second chemically oxygen terminated or H-terminated carbon-based material, said first and said second carbon-based material forming an electrode, for its use as described above, wherein said first chemically oxygen terminated or H-terminated carbon-based material constitutes the tip of an individual penetrating electrode or the penetrating electrode tips of electrode arrays and said second carbon-based material constitutes the interfacing surface between the prosthesis or implant and the glial surface of any neuronal structure.

An other object provided is the first biocompatible chemically oxygen terminated or H-terminated carbon-based material, bound to a biocompatible second chemically oxygen terminated or H-terminated carbon-based material, said first and said second carbon-based material forming an electrode, for its use as described above, wherein said peptide is from the extracellular matrix, in particular selected from the group consisting of poly-lysine, in particular poly-D-lysine, poly-ornithine, laminin or combination thereof, in particular the thickness of the peptide coating being comprised from about 0.5 μg/cm$^2$ to about 5 μg/cm$^2$.

The present invention provides a process of preparation of an electrode or needle as described above, comprising the following steps:

a. preparation of conductive biocompatible chemically oxygen terminated or H-terminated carbon-based material scaffold, b. optionally, oxidation of said H-terminated carbon-based material scaffold to obtain a first carbon-based material, c. optionally doping a second part of said chemically oxygen terminated or H-terminated carbon-based material scaffold, in particular with boron, phosphorus or nitrogen, to obtain a partially doped second part of said chemically oxygen terminated or H-terminated carbon-based material scaffold, d. coating said second part of said chemically oxygen terminated or H-terminated carbon-based material scaffold with a peptide, optionally doped, in particular a peptide from the extracellular matrix, to obtain a second chemically oxygen terminated or H-terminated carbon-based material, said first chemically oxygen terminated or H-terminated carbon-based material and said second chemically oxygen terminated or H-terminated carbon-based material constituting an electrode, in particular said peptide is selected from the group consisting of poly-lysine, in particular poly-D-lysine, poly-ornithine or laminin.

The present invention also provides an electrode according to the above description, wherein said electrode is:

(i) a planar array with a common counter electrode with the shape of a grid surrounding the stimulating electrodes, (ii) a planar electrode array with a distant counter electrode, (iii) a three-dimensional electrode, in particular a three-dimensional electrode array with a stimulation electrode surrounded by a grid again serving as a counter electrode; or (iv) a three-dimensional electrode with a distant counter electrode with a inter-electrode distance was kept at 100 μm and the well depth for the 3D models was 30 μm.

The present invention relates to the use of a first biocompatible chemically oxygen terminated or H-terminated carbon-based material, the surface of which is substantially free of any peptide coating, to promote the growth or at least the direct interfacing of adult neurons on said material without substantially promoting the growth and direct interfacing of glial cells on said material, said carbon-based material having an electrical conductivity of at least about 0.01 S·cm$^{-1}$, in particular 1 S·cm$^{-1}$, preferably 10 S·cm$^{-1}$, more preferably 100 S·cm$^{-1}$.

The expression "carbon-based material" refers to a material constituted by only carbon atoms above 95%, the remaining percents corresponding to doping species if necessary. "H-terminated carbon-based material" refers to carbon-based material as grown and "oxygen terminated carbon-based material" refers to chemically oxidized carbon-based material.

To provide diamond with semiconducting properties, third elements can be used in its matrix such as boron, phosphorous or nitrogen, at concentrations between 1 ppm and 5%. The term "biocompatible" refers to the ability of a material to perform with an appropriate host response in a specific situation without interfering or degrading the biological medium (in particular a living biological medium) in which it is used. It also refers to a non immunogenic material.

The material is named "first" because it represents a first part of a material that can be bound to another part that will be named "second" part.

In all the specifications, the expression "a first biocompatible chemically oxygen terminated or H-terminated carbon-based material" can also be named "first part of a carbon-based material" or "first part of a material" or "first part" alone and have the same meaning.

The expression "substantially free of any peptide coating" means that the material does not present a peptide coating or if present this peptide coating, in particular a peptide from the extracellular matrix, is in a ratio less than 1% in surface coverage.

The expression "promoting the growth and direct interfacing of adult neurons" means that the material allows either the neurons to develop on said material or if neurons cannot develop, at least, the material allows the adhesion of said neurons on said material.

By adult neurons, it is referred to neurons previously collected from animals older than 1 months while embryonic neurons are previously collected on embryos and area therefore still not mature.

The term "adult" can also be replaced by "mature" or "differentiated" in this specification.

The expression "without substantially promoting the growth and direct interfacing of glial cells on said material" means that said material presents a ratio of glial cells grown on it or adhered on it of less than 5% in surface coverage.

The material used in the invention exhibits electrical conductivity and therefore, cannot be constituted of glass exclusively.

Said conductivity is at least 0.01 S·cm$^{-1}$ or is equal or higher than 0.01 S·cm$^{-1}$, in particular said conductivity is 1 S·cm$^{-1}$ and advantageously is 10 and more advantageously is 100 S·cm-1 or higher for material such as diamond.

In an advantageous embodiment, said conductivity is comprised from 10 S·cm$^{-1}$ to 1000 S·cm$^{-1}$, preferably from 100 S·cm$^{-1}$ to 500 S·cm$^{-1}$ and more preferably is equal to 100 S·cm$^{-1}$.

However, for a material such as graphene, the conductivity is much higher and can be as high as about $1^E4$ S·cm$^{-1}$.

The inventors have unexpectedly found that a conductive carbon-based material that is not coated with a peptide, could both allows the growth or adhesion or interfacing of adult neurons on it, as well as also prevents the growth or adhesion or interfacing of glial cells on said material, avoiding thus the gliosis, that is the proliferation of glial cells, and the loss of functionality of said material, in particular the stimulating function of neurons by said material thanks to its conductivity.

In an advantageous embodiment, the present invention relates to the use of a first biocompatible chemically oxygen terminated or H-terminated carbon-based material, as defined above, wherein said material is selected from the group consisting of nanocrystalline diamond which is doped by either boron, phosphorus or nitrogen, to become a semiconductor, or graphene, nanotubes, or nanotubes on diamond.

By "nanocrystalline diamond" is meant a layer which composition is pure diamond exhibiting a grain structure, where the grain size ranges between 5 and 100 nm in average.

By "polycrystalline diamond" is meant a layer which composition is pure diamond exhibiting a grain structure, where the grain size ranges between 100 nm and 50 micrometers.

By "graphene" is meant an insulated one-atom-thick planar sheet of sp2-bonded carbon atoms that composes graphite.

By "nanotubes" is meant a hollow cylindrical molecule made of sp2-bonded carbon atoms that composes graphite, rolled over itself to form a cylinder. Nanotubes can be composed by one (single wall) or several (multiwall) carbon tubes with effect on their electronic properties.

By "nanotubes on diamond" is meant a structure where nanotubes are grown on a diamond substrate.

Materials such as diamond are not semiconductor as such and necessitate to be doped to become semiconductor. However, materials such as graphene are semiconductor in themselves and do not necessitate to be doped.

In an advantageous embodiment, the present invention relates to the use of a first biocompatible chemically oxygen terminated or H-terminated carbon-based material, as defined above, wherein said first chemically oxygen terminated or H-terminated carbon-based material is different from nanodiamond powder, in particular on nanocrystalline diamond or on polycrystalline diamond or on other materials, or from nanocrystalline diamond within which nanotubes are partially embedded.

In this embodiment, material such as powder of monodispersed nanodiamond powder or nanocrystalline diamond within which nanotubes are partially embedded are therefore excluded from the scope of the invention in some aspects.

Nevertheless, it must be noted that nanotubes on diamond that are different from nanocrystalline diamond within which nanotubes are partially embedded, are not excluded form the scope of the invention.

In an advantageous embodiment, the present invention relates to the use of a first biocompatible chemically oxygen terminated or H-terminated carbon-based material, as defined above, wherein said adult neurons are found in tissues selected from the group consisting of the retina, thalamus, cortex, vestibular system, cochlea, brain stem, midbrain, colliculus, subthalamic nucleus, globus pallidus interna, zona incerta, pallidofugal fibers, periaqueductal gray, periventricular gray, internal capsule, ventral posterolateral nucleus and ventral posteromedial nucleus, subgenual cingulate gyrus, nucleus accumbens, ventral capsule/ventral striatum, inferior thalamic peduncle, lateral habenula vagus nerve, afferent nerves, spinal cord, large dorsal columns, nerves controlling muscle activity such as those for locomotion or sphincter opening.

In an advantageous embodiment, the present invention relates to the use of a first biocompatible chemically oxygen terminated or H-terminated carbon-based material, as defined above, wherein said first carbon-based material is bound to a biocompatible second chemically oxygen terminated or H-terminated carbon-based material, similar to, identical to or different from said first carbon-based, said first and said second carbon-based material forming an electrode, said second carbon-based material presenting a peptide coating, in particular a peptide from the extracellular matrix, to promote the growth and at least the direct interfacing of adult glial cells.

The second carbon-based material corresponds thus to the second part above defined and the binding of the first part as defined above and the second part as defined above constitutes an electrode.

In all the specification, the expressions "a second biocompatible chemically oxygen terminated or H-terminated carbon-based material" can also be named "second part of a carbon-based material" or "second part of a material" or "second part" alone and have the same meaning.

Said first and second parts can be similar or identical with respect to the material, that is they are constituted by the same material, with the proviso that the first part is always not coated with a peptide coating and the second part is always coated with a peptide coating, and provided that the electrode thus constituted could still be conductive.

Said first and second parts can be different with respect to the material, that is they are constituted by the different materials, with the proviso that the first part is always not coated with a peptide coating and the second part is always coated with a peptide coating, and provided that the electrode thus constituted could be still conductive.

The inventors have thus found that the binding of the two parts of a carbon-based material, similar, identical or different, could both,
1) promote, due to the first part, the growth or adhesion or interfacing of adult neurons on it, while preventing the growth or adhesion or interfacing of glial cells on said first part, avoiding thus the gliosis, that is the proliferation of glial cells, and the loss of functionality of said first part,
2) promote, due to the second part, the growth of glial cells locally in the environment of said second part but not in the first part, leading thus to a synergy between the two parts of said carbon-based material as glial cells are essential for the survival of neurons.

In an advantageous embodiment, said first carbon-based material bound to said second carbon-based material is stable for at least six months.

The term "stable" means that said first carbon-based material bound to said second carbon-based material always constitute a functional electrode after six months or more.

Another advantage of the invention is to provide an electrode having a life time higher than the one of the electrodes of the prior art due to the constitution in both parts of said electrode, avoiding thus the gliosis that is likely to occur to reconstitute the continuity in the external glial barrier preventing any tissue change in ionic homeostasis, and the loss of the electrode functionality that leads to the frequent change of the electrode in the prior art.

Both first and second parts of material can be laid on a soft support (polyimide, parylene . . . ) or a rigid substrate made of silicon, glass, quartz or metal substrates (Platinum alloys or Titanium allows, Gold or Titanium, silicon carbide, . . . ).

In an advantageous embodiment, the present invention relates to the use of a first biocompatible chemically oxygen terminated or H-terminated carbon-based material, as defined above, having a first carbon-based material bound to a biocompatible second chemically oxygen terminated or H-terminated carbon-based material, similar to, identical to or different from said first carbon-based, wherein said second chemically oxygen terminated or H-terminated carbon-based material is selected from the group consisting of nanocrystalline diamond which is doped in particular with boron, in particular a boron-doped hydrogen terminated diamond or oxidized diamond, graphene or nanotubes, in particular diamond grafted with nanotubes.

In an advantageous embodiment, the present invention relates to the use of a first biocompatible chemically oxygen terminated or H-terminated carbon-based material, as defined above, having a first carbon-based material bound to a biocompatible second chemically oxygen terminated or H-terminated carbon-based material, similar to, identical to or different from said first carbon-based, wherein said first carbon-based material and said second carbon-based material are similar or identical.

Thus in this embodiment, both parts of the carbon-based material are constituted with the same material, the first part being not coated and the second part being coated.

In an advantageous embodiment, the present invention relates to the use of a first biocompatible chemically oxygen terminated or H-terminated carbon-based material, as defined above, having a first carbon-based material bound to a biocompatible second chemically oxygen terminated or H-terminated carbon-based material, similar to, identical to or different from said first carbon-based, wherein said electrode is shaped like a penetrating electrode, such as a penetrating needle, in particular a tri-dimensional needle, or is positioned on a penetrating support, which can be shaped like a needle, in particular a tri-dimensional needle.

By "penetrating electrode" is meant an electrode liable to penetrate a tissue such as a tissue defined above.

As an example, said electrode can penetrate the retina in order to stimulate the neurons of the retina in which photoreceptors have been degenerated in case of pathologies such as age-related macular degeneration (AMD) or retinitis pigmentosa.

A penetrating electrode in the prior art has the disadvantage of destroying the glial barrier of the tissue in which the electrode penetrates because neuronal tissues are always surrounded by a glial cell layer acting as a physical barrier.

Another advantage of the invention is to provide a penetrating electrode that solves this problem as the electrode is constituted of a second part liable to promote the growth of glial cells and thus holes created by the penetrating needles or electrodes can be rapidly sealed.

An adequate sealing at the basis of the electrode prevents further gliosis around the electrode tips where stimulating electrodes are displaced. Direct contact or close distance between neurons and electrodes will provide the best electrical stimulation with the minimum current intensities.

Said electrode can be a needle.

In an advantageous embodiment, a needle or an electrode is tri dimensional. For the purpose of the present invention, the terms "tri dimensional" means that the said needle or electrode is not planar or flat and is defined according to three dimensions: length, and thickness (width and height). A tri dimensional (3D) device means a device with a thickness (e. g. a width) of more than 2 micrometer.

In the present invention, an electrode or a needle may have the shape of a cylinder or of a polytope. A polytope is a finite region of n-dimensional space bounded by hyperplanes. In particular, a polytope is a three-dimensional figure formed by at least six parallelograms. In particular embodiments said polytope or cylinder is planar of flat, said needle or said electrode being tri dimensional and is square or rectangular with the greatest length comprises from 5 µm to 1 mm and one of the thicknesses is less than 2 µm.

In a particular embodiment, said electrode is defined according to its length and diameter.

In another advantageous embodiment, said electrode could be a planar electrode, or a planar needle. It is well understood that a flat or a planar electrode or a flat or a planar needle means a three-dimensional figure wherein the dimension defining (width) thickness is less than 2 micrometer or from 2 to 0.001 micrometer.

In particular embodiments the present invention provides:
(i) a planar array with a common counter electrode with the shape of a grid surrounding the stimulating electrodes,
(ii) a planar electrode array with a distant counter electrode,
(iii) a three-dimensional electrode array with a stimulation electrode surrounded by a grid again serving as a counter electrode; and
(iv) a three-dimensional electrode with a distant counter electrode with a inter-electrode distance was kept at 100 µm and the well depth for the 3D models was 30 µm.

Electrodes according to the invention are either circular, oval, square or rectangular with the greatest length comprises from 5 µm to 1 mm.

Electrodes are either circular, oval, square or rectangular with the greatest length comprises from 5 µm to 1 mm.

Implants are planar whenever one of their thicknesses is below 2 µm. Implants are considered tridimensional (3D) as soon as thicknesses are greater than 2 µm. A thickness difference can separate the stimulating electrodes and either the reference electrodes or the ground grid. It can also represent walls separating electrodes and the ground surfaces. The thickness difference is greater than 2 µm and usually in a range from 20 µm to 1 mm although this thickness difference can reach several centimeters when target structures are deep inside the organ, as in the brain. The 3D structure can take different shapes from pillars, arrows, needles, wells, cavities with a cubic, polygonal, cylindrical or conic shape with all possible combinations and intermediates.

In an advantageous embodiment, the present invention relates to the use of a first biocompatible chemically oxygen terminated or H-terminated carbon-based material, as defined above, having a first carbon-based material bound to a biocompatible second chemically oxygen terminated or H-terminated carbon-based material, identical to or different from said first carbon-based, said electrode being shaped like a penetrating electrode, such as a penetrating needle, in particular a tri-dimensional needle, wherein a plurality of electrodes is combined to form an electrode array.

In an advantageous embodiment, the present invention relates to the use of a first biocompatible chemically oxygen terminated or H-terminated carbon-based material, as defined above, having a first carbon-based material bound to a biocompatible second chemically oxygen terminated or H-terminated carbon-based material, similar to, identical to or different from said first carbon-based, said electrode being shaped like a penetrating electrode, such as a penetrating needle, in particular a tri-dimensional needle, wherein a plurality of electrodes is combined to form an electrode array, wherein said electrode or electrode array is fixed on a support to form an implant or a prosthesis.

As an example and illustration, said electrode array could ultimately exhibit the conformation presented FIG. 12.

In an advantageous embodiment, the present invention relates to the use of a first biocompatible chemically oxygen terminated or H-terminated carbon-based material, as defined above, having a first carbon-based material bound to a biocompatible second chemically oxygen terminated or H-terminated carbon-based material, similar to, identical to or different from said first carbon-based, said electrode being shaped like a penetrating electrode, such as a penetrating needle, in particular a tri-dimensional needle, wherein a plurality of electrodes is combined to form an electrode array, said electrode or electrode array being fixed or not on a support to form an implant or a prosthesis, wherein said first chemically oxygen terminated or H-terminated carbon-based material constitutes the tip of an individual penetrating electrode or the penetrating electrode tips of electrode arrays and said second carbon-based material constitutes the interfacing surface between the prosthesis or implant and the glial surface of any neuronal structure.

The electrode or electrode array penetrating a tissue, the not coated first part must be the tip of said electrode to stimulate the neurone interfacing or growing on it and the second part must be the interfacing surface between the prosthesis or implant and the glial surface of any neuronal structure to promote the growth of said glial cells to seal the holes formed during the penetration and help the neurones of the first part to grow and/or survive.

The surface implant or neuroprostheses are not necessary flat, they can present well shapes with electrodes and/or returning grids in either the wells and/on the upper surface.

In arrays with penetrating electrodes, this peptide-coated carbon material could cover the basis of the penetrating structures (e.g. penetrating needles) where direct neurone interfacing is not intended or not possible due to gliosis for restoring the glial sheath continuity.

In an advantageous embodiment, the present invention relates to the use of a first biocompatible chemically oxygen terminated or H-terminated carbon-based material, as defined above, having a first carbon-based material bound to a biocompatible second chemically oxygen terminated or H-terminated carbon-based material, similar to, identical to or different from said first carbon-based, wherein said peptide is from the extracellular matrix, in particular selected from the group consisting of poly-lysine, in particular poly-D-lysine, poly-ornithine, laminin or combination thereof.

These peptides from the extracellular matrix play a supporting role in vivo that is used in vitro to promote cell attachment and therefore survival. The presence of these peptides is particularly useful for glial cell maintenance.

In an advantageous embodiment, the present invention relates to the use of a first biocompatible chemically oxygen terminated or H-terminated carbon-based material, as defined above, having a first carbon-based material bound to a biocompatible second chemically oxygen terminated or H-terminated carbon-based material, similar to, identical to or different from said first carbon-based, as defined above, wherein the thickness of the peptide coating is comprised from about 0.5 µg/cm$^2$ to about 5 µg/cm$^2$.

In an advantageous embodiment, the present invention relates to the use of a first biocompatible chemically oxygen terminated or H-terminated carbon-based material, as defined above, having a first carbon-based material bound to a biocompatible second chemically oxygen terminated or H-terminated carbon-based material, similar to, identical to or different from said first carbon-based, said electrode being shaped like a penetrating electrode, such as a penetrating needle, in particular a tri-dimensional needle, as defined above, wherein the length of said penetrating needle and/or electrode is comprised from about 10 µm to about 1 to 2 cm and the diameter is comprised from 20 µm to about 500 µm.

In function of the tissue in which the penetrating electrode must be installed, the length of said penetrating electrode will be different.

As an example, the length of said electrode for cochlea is about 1 mm and for nerves controlling muscle activity such as those for locomotion or sphincter opening is about 1 cm.

In an advantageous embodiment, the present invention relates to the use of a first biocompatible chemically oxygen terminated or H-terminated carbon-based material, as defined above, having a first carbon-based material bound to a biocompatible second chemically oxygen terminated or H-terminated carbon-based material, similar to, identical to or different from said first carbon-based, said electrode being shaped like a penetrating electrode, such as a penetrating needle, in particular a tri-dimensional needle, as defined above, wherein the length of said penetrating needle and/or electrode is comprised from about 10 µm to about 1 to 2 cm and the diameter is comprised from 20 µm to about 500 µm, as defined above, wherein the length ratio: first carbon-based material/second carbon-based material is comprised from 0.1 to 10.

In another aspect, the present invention relates to an electrode comprising a first chemically oxygen terminated or H-terminated carbon-based material to promote the growth or at least the direct interfacing of adult neurons, without substantially promoting the growth and direct interfacing of glial cells on said material, which is bound to a second biocompatible chemically oxygen terminated or H-terminated carbon-based material, similar to, identical to or different from said first carbon-based material, such as defined above, said second carbon-based material presenting a peptide coating, in particular a peptide from the extracellular matrix, to promote the growth and at least the direct interfacing of adult glial cells.

In an advantageous embodiment, the present invention relates to an electrode as defined above, wherein said second chemically oxygen terminated or H-terminated carbon-based material presents a peptide coating, in particular a peptide from the extracellular matrix to promote the growth of adult glial cells.

In an advantageous embodiment, the present invention relates to an electrode as defined above, wherein said electrode is non cytotoxic.

Neither the materials used, nor the doping or the coating are cytotoxic and thus all the compounds constituting said electrode are biocompatible and not immunogenic.

In an advantageous embodiment, the present invention relates to an electrode as defined above, which is stable for at least six months.

The term "stable" means that the electrode always functions after six months or more, that is to say that gliosis has not altered said electrode and said electrode is always liable to stimulate adult neurons of said tissues.

In an advantageous embodiment, the present invention relates to an electrode as defined above, wherein said first and second carbon-based materials are selected from the group consisting of nanocrystalline diamond which is doped by either boron, phosphorus or nitrogen, to become a semiconductor, or graphene, nanotubes, or nanotubes on diamond.

In an advantageous embodiment, the present invention relates to an electrode as defined above, wherein said first chemically oxygen terminated or H-terminated carbon-based material and said second chemically oxygen terminated or H-terminated carbon-based material are similar or identical.

In an advantageous embodiment, the present invention relates to an electrode as defined above, wherein said electrode is shaped like a penetrating electrode, such as a penetrating needle, in particular a tridimensional needle, or is positioned on a penetrating support, which can be shaped like a needle, in particular a tri-dimensional needle.

In an advantageous embodiment, the present invention relates to an electrode as defined above, wherein a plurality of electrodes is combined to form an electrode array.

In an advantageous embodiment, the present invention relates to an electrode as defined above, wherein said electrode or electrode array is fixed on a support to form an implant or a prosthesis.

In an advantageous embodiment, the present invention relates to an electrode wherein said electrode is shaped like a penetrating electrode, or wherein a plurality of electrodes is combined to form an electrode array, as defined above, wherein said first carbon-based material constitutes the tip of an individual penetrating electrode or the penetrating electrode tips of electrode arrays and said second carbon-based material constitutes the interfacing surface between the prosthesis or implant and the glial surface of any neuronal structure.

In an advantageous embodiment, the present invention relates to an electrode, as defined above, wherein said peptide is selected from the group consisting of poly-lysine, in particular poly-D-lysine, poly-ornithine or laminin.

In an advantageous embodiment, the present invention relates to an electrode, as defined above, wherein the thickness of the peptide coating is comprised from about 0.5 µg/cm² to about 5 µg/cm².

In an advantageous embodiment, the present invention relates to an electrode, as defined above, wherein the length of said penetrating needle and/or electrode is comprised from about 10 µm to about 1 to 2 cm and the diameter of said electrode is comprised from 20 µm to about 500 µm.

In an advantageous embodiment, the present invention relates to an electrode, as defined above, wherein the length ratio: first carbon-based material/second carbon-based material is comprised from 0.1 to 10.

In an advantageous embodiment, the present invention relates to an electrode, as defined above, wherein said first chemically oxygen terminated or H-terminated carbon-based material is different from nanodiamond powder, in particular on nanocrystalline diamond or on polycrystalline diamond or on other materials, or from nanocrystalline diamond within which nanotubes are partially embedded.

In this embodiment, material such as powder of monodispersed nanodiamond powder or nanocrystalline diamond within which nanotubes are partially embedded are therefore excluded from the scope of the invention in some aspects.

Nevertheless, it must be noted that nanotubes on diamond that are different from nanocrystalline diamond within which nanotubes are partially embedded, are not excluded form the scope of the invention.

In another aspect, the present invention relates to a process of preparation of an electrode as defined above, comprising the following steps:
 a. preparation of conductive biocompatible chemically oxygen terminated or H-terminated carbon-based material scaffold,
 b. optionally, oxidation of said H-terminated carbon-based material scaffold to obtain a first carbon-based material,
 c. optionally doping a second part of said chemically oxygen terminated or H-terminated carbon-based material scaffold, in particular with boron, phosphorus or nitrogen, to obtain a partially doped second part of said chemically oxygen terminated or H-terminated carbon-based material scaffold,
 d. coating said second part of said chemically oxygen terminated or H-terminated carbon-based material scaffold with a peptide, optionally doped, in particular a peptide from the extracellular matrix, to obtain a second chemically oxygen terminated or H-terminated carbon-based material, said first chemically oxygen terminated or H-terminated carbon-based material and said second chemically oxygen terminated or H-terminated carbon-based material constituting an electrode.

The first step a. is carried out depending on the material used and if it necessitates to be doped to become conductive such as diamond.

Thus, in the case of diamond doping is carried out at the same time, in particular with boron, phosphorus or nitrogen.

In the case of graphene, doping is not carried out.

Diamond synthesis is commonly performed using CVD (chemical vapour deposition) reactors where a microwave or RF or hot filament excitation enables the dissociation of species in a gas phase to initiate the growth of diamond on a hot substrate. The technique requires precursor gases, usually a carbon supply (eg. methane) as well as hydrogen and/or Argon. The growth occurs typically between 500 and 1000° C., thus too high for conventional growth on soft polymer substrates, as usually preferred for the fabrication of soft medical prosthesis implants. To fabricate soft implants, the technique thus requires to deposit CVD diamond on a rigid substrate made of silicon, glass, or metal substrates, on which a sacrificial layer is prepared (glass, aluminium, or other materials can successfully be used). After growth of the diamond layers, and subsequent patterning of its growth in the shape of the future electrodes, the wafer can be coated with subsequent polymer using conventional low temperature processes. Then, the lift off from the sacrificial layer prepared prior to the diamond growth will enable the diamond on polymer release thus the fabrication of the soft implants. This has been described in details in FR2960787.

Further, from preliminary processing of the substrate wafer, prior to diamond growth, it is possible to fabricate moulds prior to the fabrication of soft implants, thus enabling 3D geometries to be obtained. The processing of the initial wafer can take the form of cavities, to lead to protruding diamond electrodes on the final implants. If the aspect ratio is high, the approach leads to 3D needles that are of high benefit for prosthesis electrode fabrication as presented in this invention. Further to moulds, it is also possible to start from 3D processed substrates exhibiting a high surface roughness at a micrometer or lower scale (thus to enhance the electrode roughness), a technique that enables to improve the capacitance of the electrodes due to the increase in surface ratio.

If the growth is performed using multiple steps, either overlaying or distributed in space, and involving doped or undoped layers, it becomes possible to mix within the final diamond neuroprosthesis regions of high conductivity with regions of low conductivity.

The second step b is carried out if the material need to be oxidised to obtain a first oxygen terminated carbon-based material from a first H-terminated carbon-based material.

The oxygen terminated surface can be prepared under various conditions such as annealing in air or oxygen above 400° C., or chemically in hot (>80° C.) strongly oxidizing acidic baths or also exposure to an oxygen plasma generated under RF or MW excitation. Similarly, hydrogen termination is also prepared while exposing the carbon surface to a short (from a few seconds to 1 hour) plasma treatment using microwave, RF or hot filament techniques in hydrogen rich environment in order to modify the surface termination either H-terminated or O-terminated, according to the interests for selectively prepared regions that will be preferentially preferred by tissues and cell growth.

Similarly, the resulting nanocrystalline or polycrystalline diamond implant can be used for subsequent growth of carbon nanotubes, using conventional techniques in RF plasma reactors, or for graphene sheets to be laid on its surface to benefit from its material properties. In an advantageous embodiment, the present invention relates to a process of preparation of an electrode as defined above, wherein said first part of said chemically oxygen terminated or H-terminated carbon-based material scaffold is doped with boron, phosphorus or nitrogen.

In an advantageous embodiment, the present invention relates to a process of preparation of an electrode as defined above, wherein said partially doped first part of chemically oxygen terminated or H-terminated carbon-based material scaffold is oxidized.

In an advantageous embodiment, the present invention relates to a process of preparation of an electrode as defined above, wherein said peptide is selected from the group consisting of poly-lysine, in particular poly-D-lysine, poly-ornithine or laminin.

In an advantageous embodiment, the present invention relates to a process of preparation of an electrode as defined above, wherein said first part of chemically oxygen terminated or H-terminated carbon-based material is nanocrystalline diamond, polycrystalline diamond, or graphene.

In an advantageous embodiment, the present invention relates to a process of preparation of an electrode as defined above, wherein said second part of chemically oxygen terminated or H-terminated carbon-based material is nanocrystalline diamond, polycrystalline diamond, or graphene.

In an advantageous embodiment, the present invention relates to a process of preparation of an electrode as defined above, wherein said first and/or second chemically oxygen terminated or H-terminated carbon-based material is different from monodispersed nanodiamond powder on nanocrystalline diamond or on polycrystalline diamond or on other materials or from nanocrystalline diamond within which nanotubes are partially embedded.

In this embodiment, material such as powder of monodispersed nanodiamond powder or nanocrystalline diamond within which nanotubes are partially embedded are therefore excluded from the scope of the invention in some aspects.

Nevertheless, it must be noted that nanotubes on diamond that are different from nanocrystalline diamond within which nanotubes are partially embedded, are not excluded form the scope of the invention.

In another aspect, the present invention relates to the use of an electrode, as defined above, for the implementation of an implant or a prosthesis liable to promote the growth of adult neurons or at least the direct interfacing of adult neurons and to stimulate said adult neurons.

In an advantageous embodiment, the present invention relates to the use of an electrode, as defined above, wherein said neurons are retinal neurons and said implant is a retinal implant.

In an advantageous embodiment, the present invention relates to the use of an electrode, as defined above, wherein said electrode further comprises glial cells.

DESCRIPTION OF FIGURES

FIGS. 1A to 1G present the cell labellings and cell counting of glass and diamond substrates with or without peptide coating.

FIGS. 1A to 1E present the cell labellings on glass (A-B) and diamond (C-F) substrates with (A, C, E) and without peptide coating (B, D, F). Glial cells and bipolar cells are identified in mixed retinal cell cultures, with an anti-GFAP (green: star or wire form) and an anti-Goα (red: dot form) antibody, respectively.

FIG. 1A: peptide-coated glass;
FIG. 1B: non coated glass;
FIG. 1C: peptide-coated H-(hydrogen) terminated diamond;
FIG. 1D: not coated H-terminated diamond;
FIG. 1E: peptide-coated O-(oxygen) terminated diamond;
F: not coated O-terminated diamond.

FIGS. 1G and 1H present the cell counting on the different substrates of the neuronal bipolar cells (G) and macroglial cells (H). Note that the decrease in glial cells on uncoated substrates is greater than that of bipolar cells. Scale bar, 50 µm.
x-axis: left three histograms: coated: from left to right: glass, H-diamond and O-diamond.
Right three histograms: non coated: from left to right: glass, H-diamond and O-diamond.
y-axis: number of cells

FIG. 2A: coated glass;
FIG. 2B: not coated glass;
FIG. 2C: coated O-terminated diamond;
FIG. 2D: not coated O-terminated diamond.
FIG. 2E: Cell quantification of viable retinal ganglion cells at 6 days in vitro normalized to their number at 1 day in vitro.
FIG. 2F: Quantification of neurite outgrowth on pure retinal ganglion cells (neurite length in µm) at 6 days in vitro.

The cell survival is significantly higher on both glass and diamond without any peptidic coating and the neurite outgrowth is greater on uncoated diamond and glass than on the coated substrates, very significantly. (means±s.e.m. from n=4 experiments, 3 samples/group/experiment). Variance analysis was performed by a two-way ANOVA followed by a Bonferroni post-hoc test (***$p<0.001$, *$p<0.05$). Scale bar, 50 µm.

FIGS. 3A to 3D present the distinctive glial and neuronal preference for diamond using peptide-patterned substrates. Pure postnatal (p7) retinal ganglion cells (RGCs) on a peptide-patterned glass (A) or a peptide-patterned O-terminated diamond substrates (B). RGCs are revealed by their anti-NF200 immunolabelling (red fluorescence) on the peptide pattern (green: diagonal matrix for A and horizontal-vertical matrix for B)
(C). Mixed retinal cell culture showing the glial preference for the peptide pattern on diamond. (D) Quantification of the peptide pattern surfaces on glass and diamond with the RGC overlap on these peptide patterns. (means±s.e.m, n=4 experiments).
x-axis: from left to right: glass, patterned glass, O-terminated diamond, patterned O-terminated diamond
y-axis: Percentage of RGC area colocalized with the pattern:

Variance analysis was performed by a two-way ANOVA followed by a Dunns post-hoc test (***p<0.001). The scale bar represents 50 µm.

Figure 1:
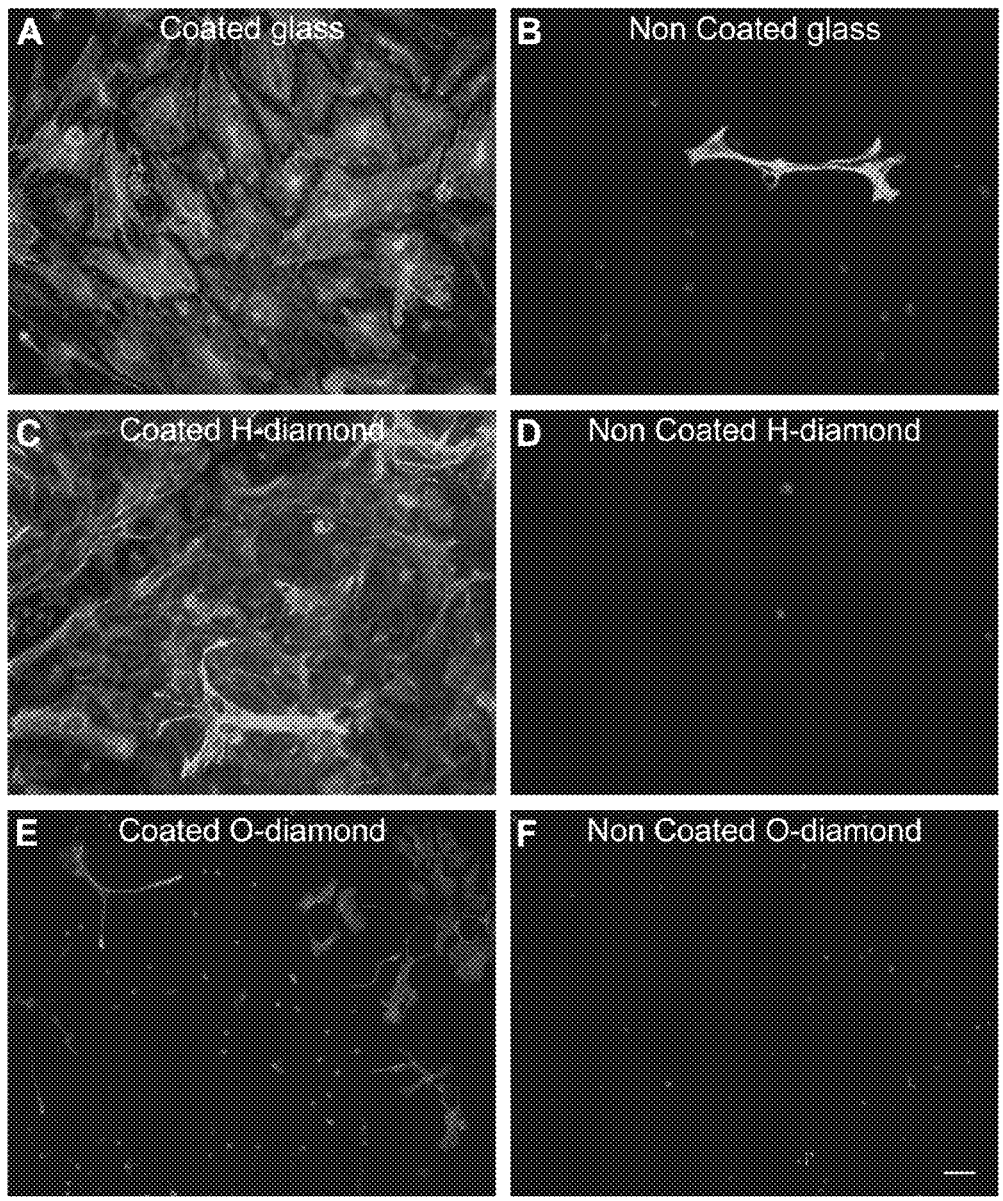
Figure 1:
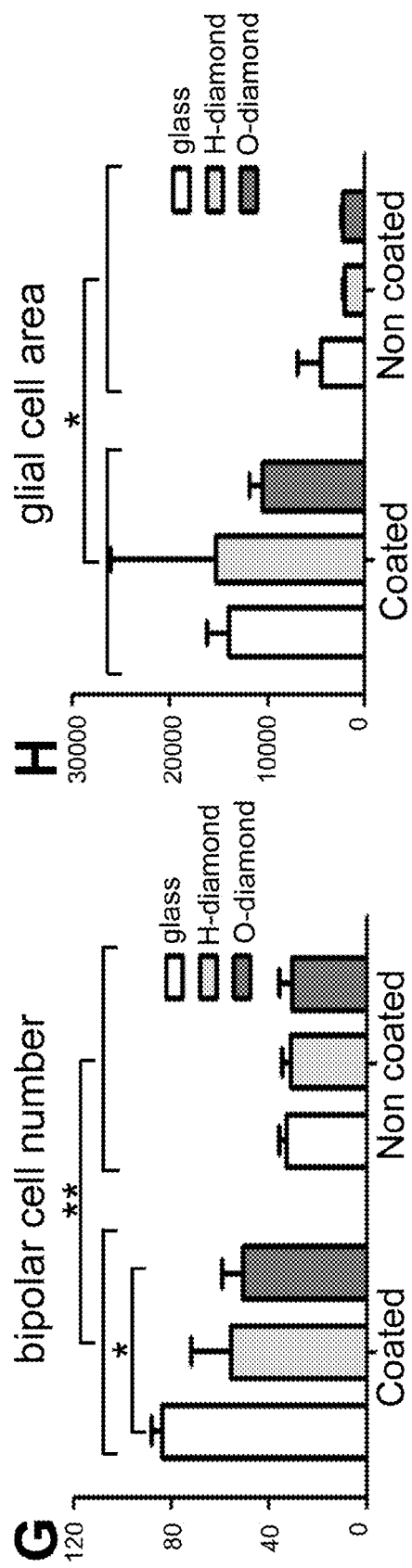
Figure 2:
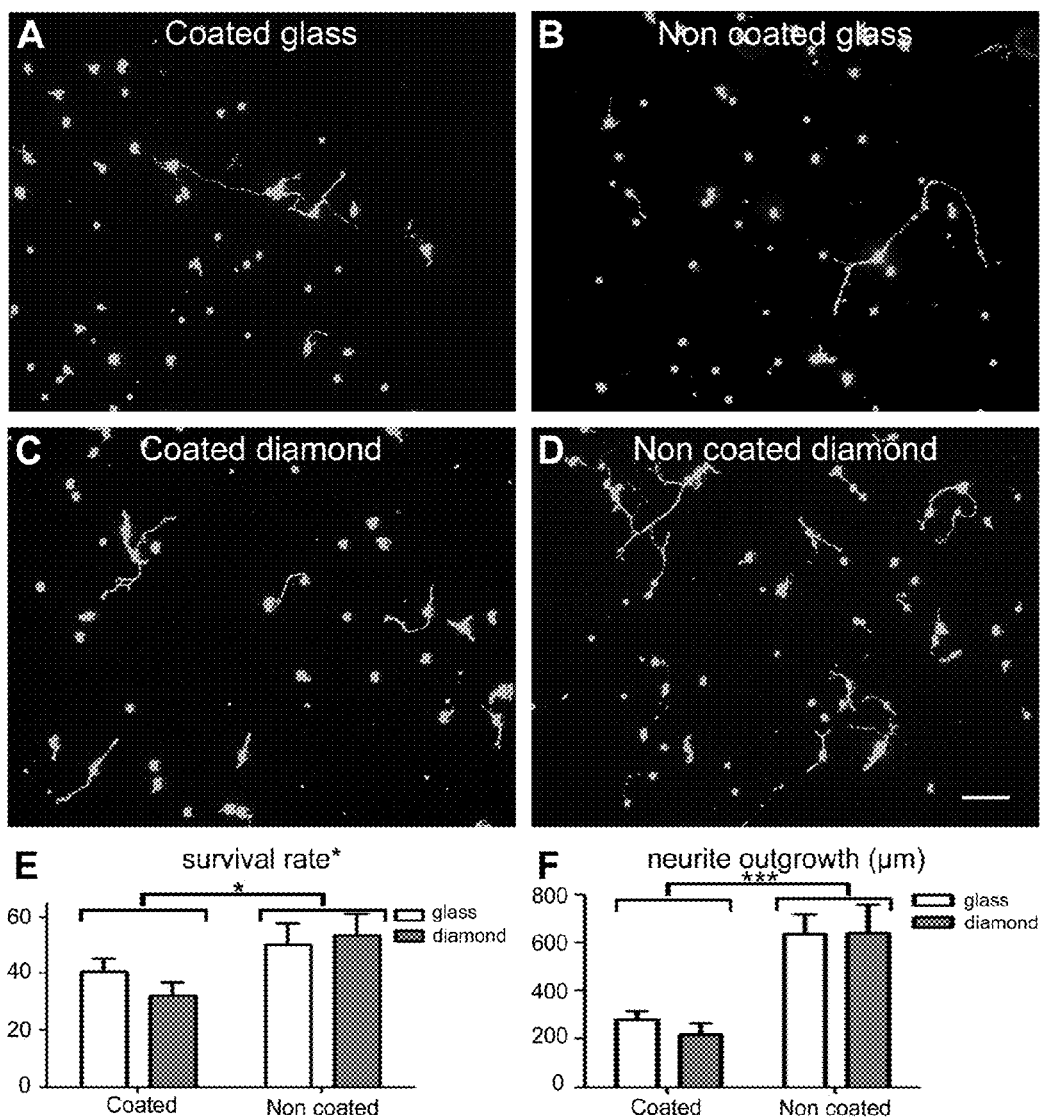
FIGS. 2A to 2F present the survival of pure adult retinal ganglion cell neurons on O-terminated diamond and glass. Viability of pure adult Retinal Ganglion Cell on glass (A-B) and diamond substrates (C-D) with (A, C) or without peptide coating (B, D).
Figure 3:
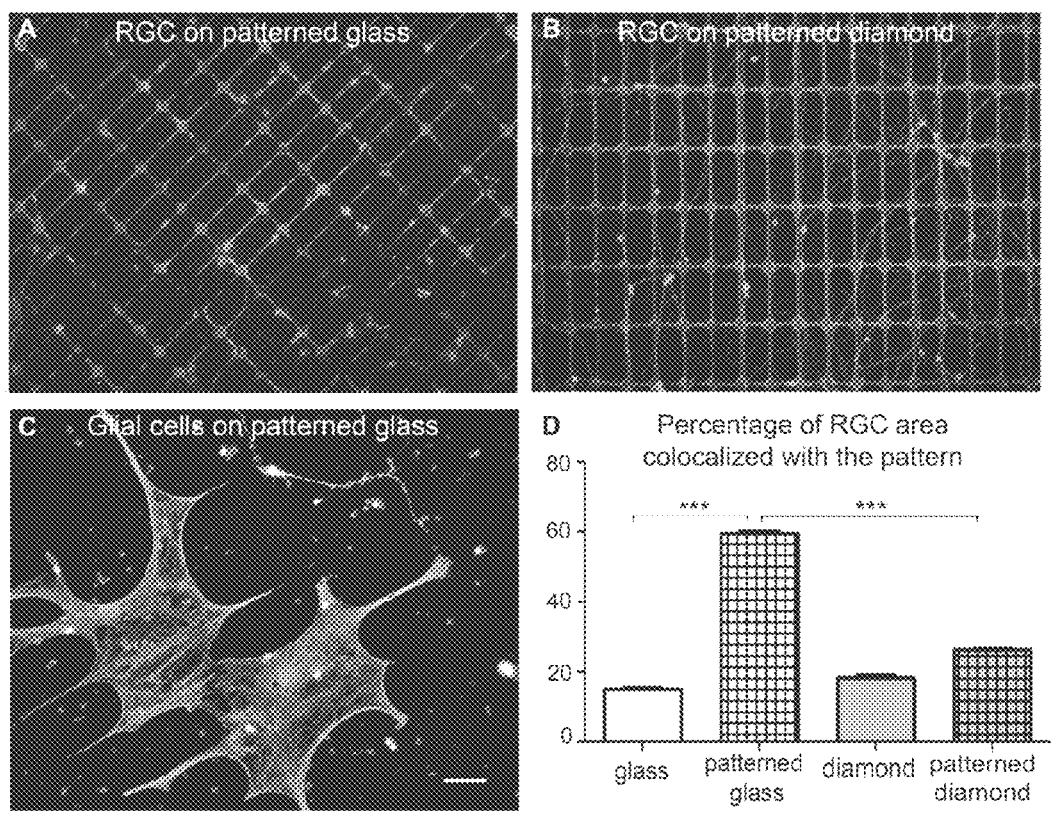
Figure 4:
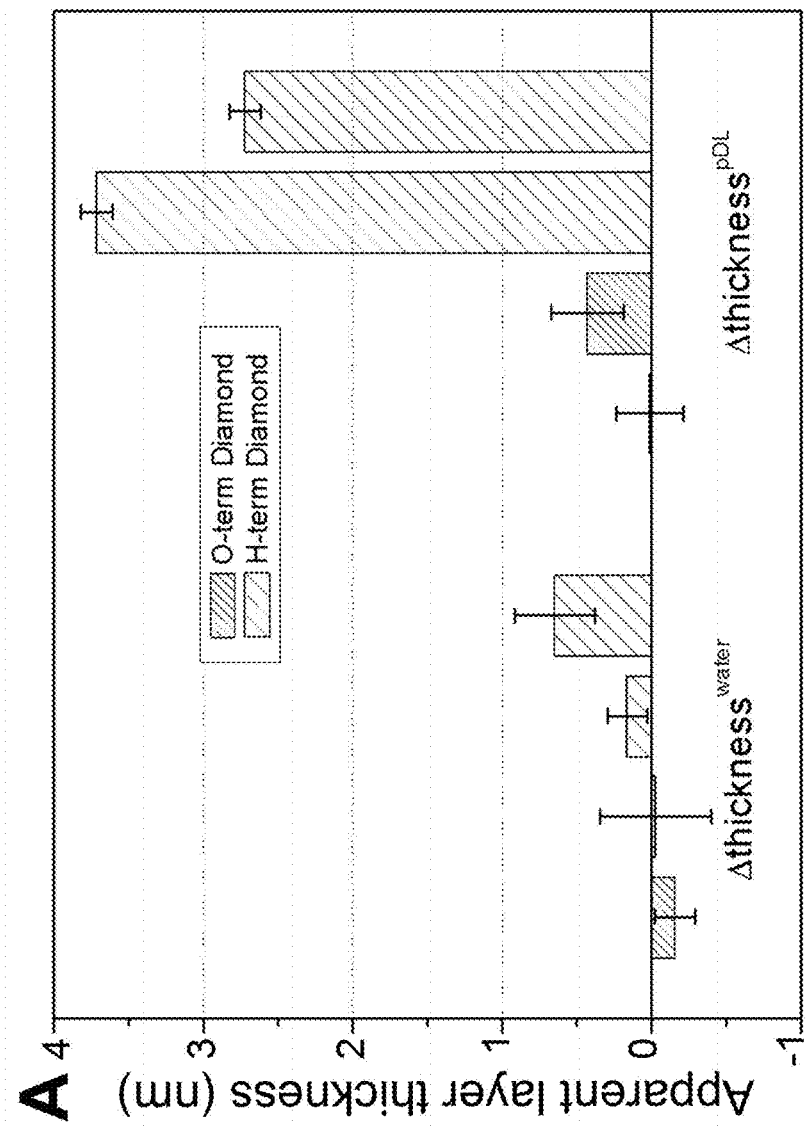
Figure 4:
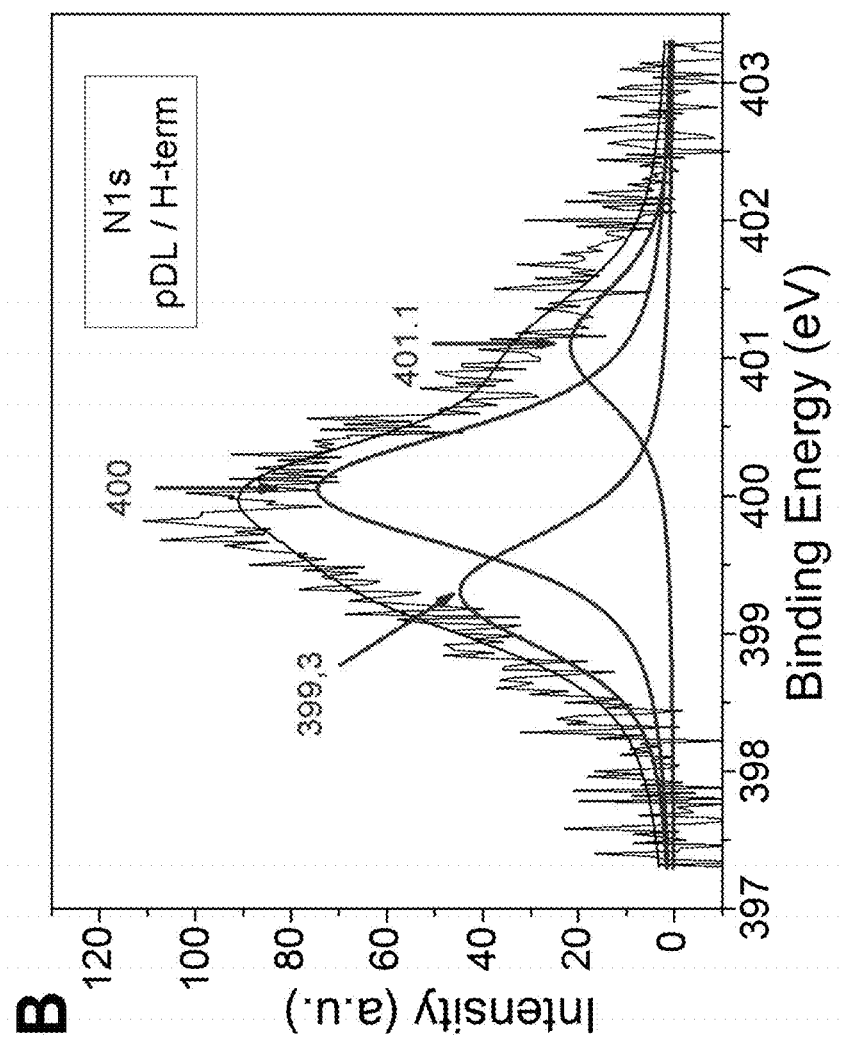
Figure 5:
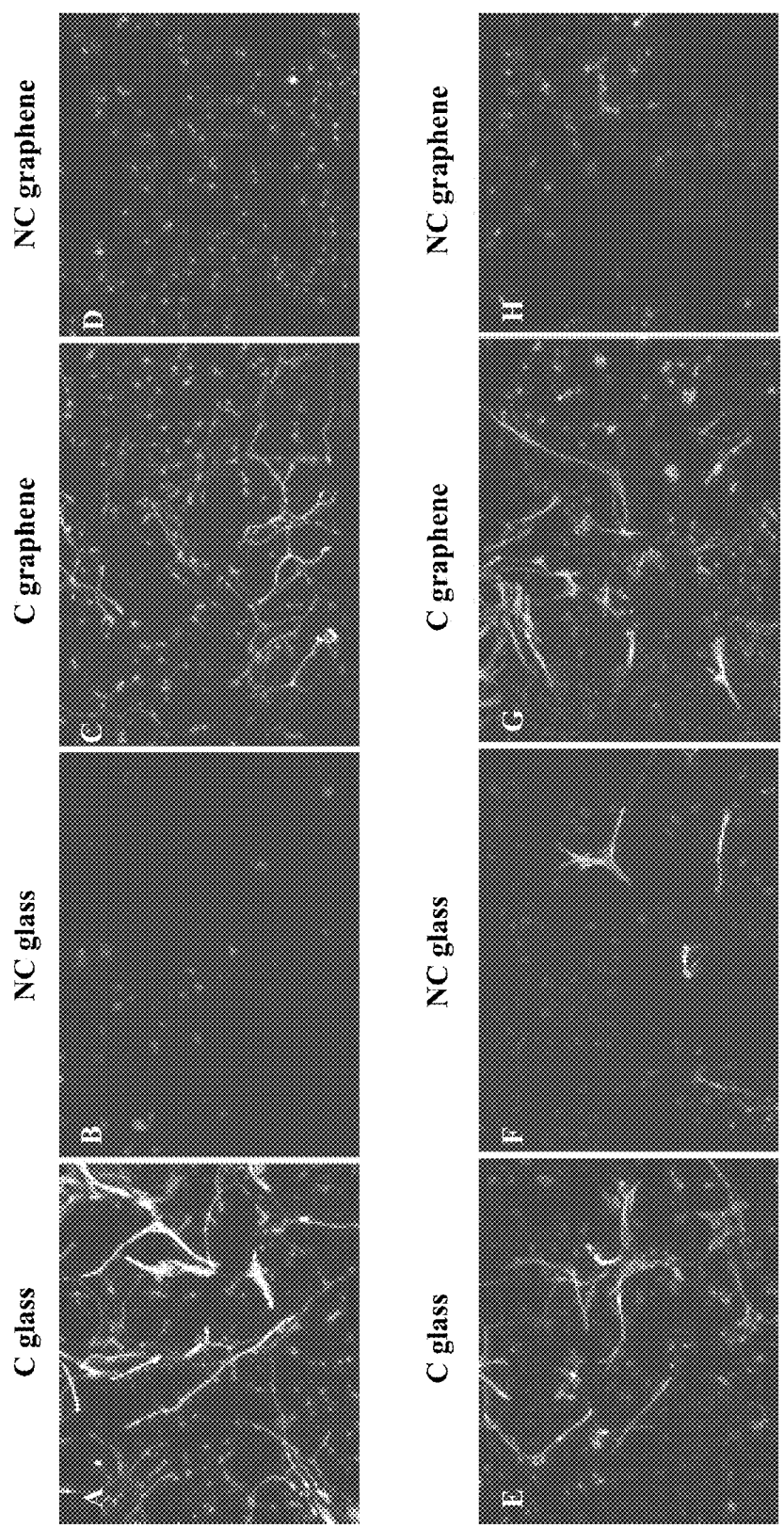

FIGS. 4A to 4B represent a characterization of the Poly-D-lysin coating on diamond.

FIG. 4A: Ellipsometry measurements on two H-terminated and two O-terminated diamond samples. Variation of apparent diamond thickness (y-axis: nm) measured by ellipsometry after 45-minute incubation of water or poly-D-lysine (pDL).

x-axis:
left: Δ thickness (water): from left to right: O-terminated diamond; O-terminated diamond; H-terminated diamond; H-terminated diamond;
right: Δ thickness (pDL): from left to right: O-terminated diamond; O-terminated diamond; H-terminated diamond; H-terminated diamond;

FIG. 4B: XPS spectrum on Hydrogen-terminated diamond surface. N1s core level of poly-D-lysine coated H-terminated diamond. Data are expressed as means±s.e.m. from n=3 experiments.

x-axis: Binding energy (eV)
y-axis: Intensity (a. u.)

FIGS. 5A to 5H present the mixed (adult) retinal cell culture on graphene & glass fixed at 6 days in vitro.

FIG. 5A to 5D: NBA+: from left to right with coated glass, non coated glass, coated graphene and non coated graphene.

FIGS. 5E to 5H: NBA, 10% serum: from left to right with coated glass, non coated glass, coated graphene and non coated graphene.

Immunostaining: anti-Goalpha for bipolar cells (dot form)/ anti-GFAP for glial cells (star or wire form), 3 samples for each condition FIGS. 6A to 6H present the survival of pure adult retinal ganglion cells (8-week old) on graphene and glass, either bare or coated with poly-D-lysine and laminin.

FIG. 6A to 6D: calcein staining, visualized by epifluorescence, of adult RGC on graphene and glass, both coated and bare;

FIGS. 6E to 6H represent, respectively, the quantification of the cell survival (ratio of survival between 6 div and 1 div in percentage), mean cell body area ($µm^2$), total outgrowth (µm) and total processes for both graphene and glass, coated and bare (from left to right). Data are expressed as means±s.e.m. from n=4 independent experiments. **p<0.01, *p<0.05; Two-way ANOVA followed by a Bonferroni post-hoc test. The scale bar represents 50 µm.

FIGS. 7A to 7J represent the survival of pure new-born retinal ganglion cells (p7) on graphene, glass, and sapphire either bare or coated with poly-D-lysine and laminin.

FIGS. 7A to 7F: calcein staining, visualized by epifluorescence, of p7 RGC on graphene, sapphire and glass, both coated and bare;

FIGS. 7G to 7J: quantification of the number of cells, the mean cell body area ($µm^2$), the total outgrowth (µm) and the total number of processes for graphene, sapphire and glass, both coated and bare (from left to right). Results are expressed as means±s.e.m. from n=4 independent experiments.

*p<0.001, p<0.01, *p<0.05; Two-way ANOVA followed by a Bonferroni post-hoc test. The scale bar represents 50 µm.

FIGS. 8A to 8F: Pure new-born retinal ganglion cells (p7) cultured on sapphire/graphene linear patterns. Differential interference contrast (DIC) images (FIGS. 8*a-b*) and fluorescence images (FIGS. 8*d-e*) representing different situations observed for the neurite outgrowth on the graphene lines.

Figure 10:
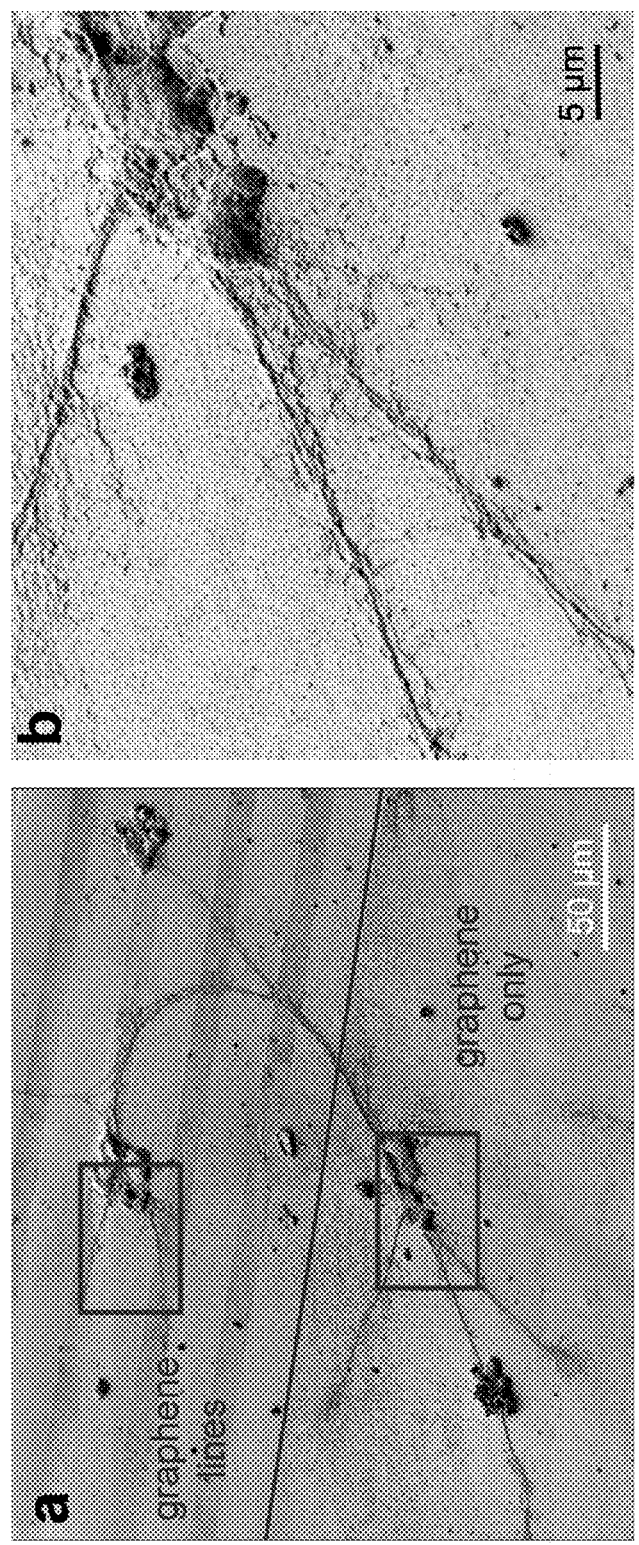

In the DIC images, graphene regions (10 µm-wide stripes) appear darker than sapphire areas (20 or 30 µm-wide stripes). DIC image (FIG. 8*c*) of cell aggregates located at the edge between patterned and unpatterned areas. The colored scanning electron microscope image (FIG. 8*f*), with graphene regions colored in red, corresponds to the region of the 3-cell aggregate marked in (FIG. 8*c*) (see also FIG. 10A to 10B).

FIGS. 9A to 9D present the characterization of CVD graphene.

Figure 9:
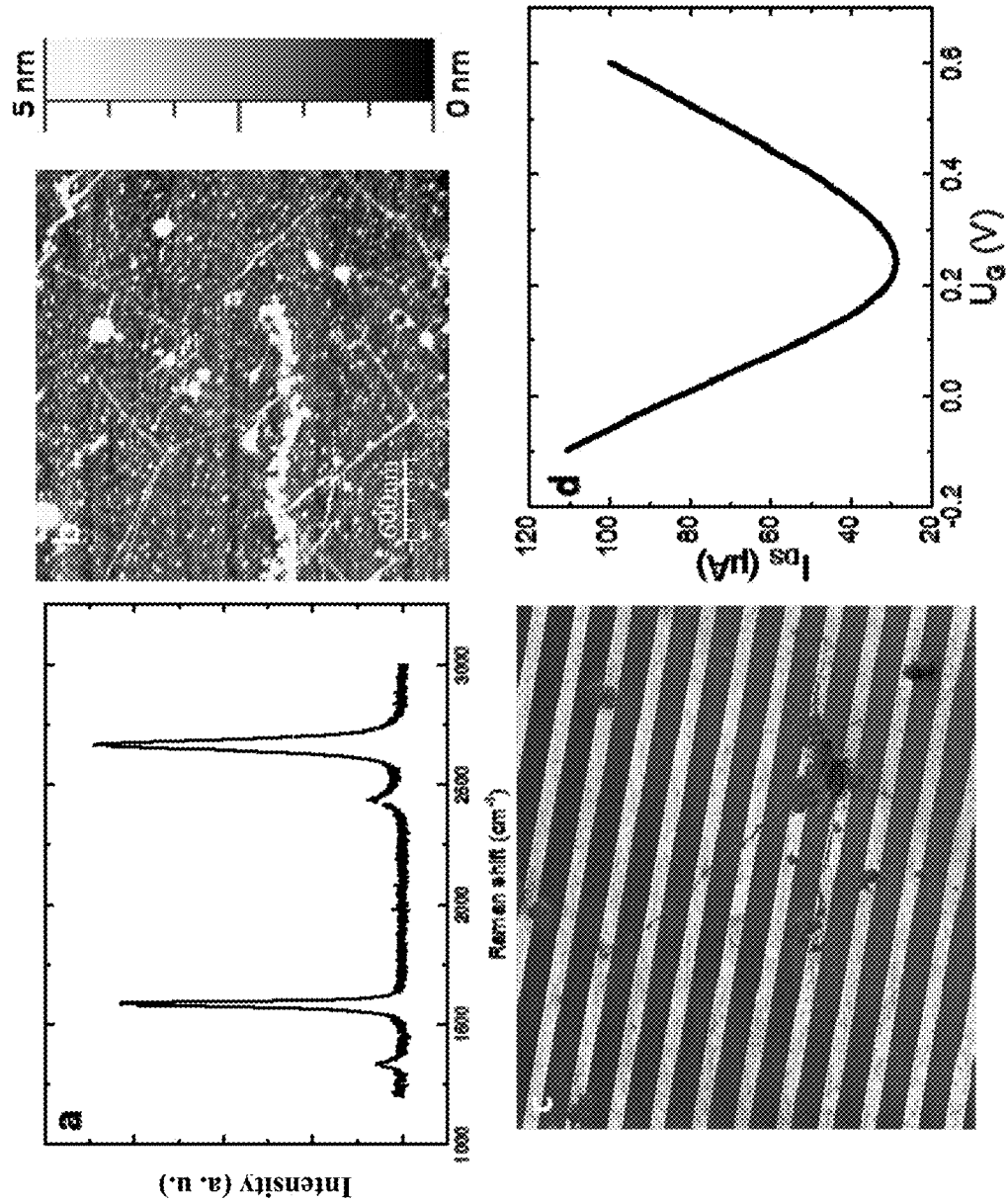

FIG. 9*a*: Raman spectrum of the CVD graphene used in this work. Clear G and 2D peaks are observed confirming the presence of graphene. The ratio of the 2D to the G peak and the Lorentzian shape of the peaks indicate a high surface coverage by single layer graphene. The small D peak suggests a rather low defect density.

FIG. 9*b*: Atomic force micrograph. The typical wrinkles are a clear indication for graphene. Punctual residual dirt from the transfer process can still be seen.

FIG. 9*c*: Scanning electron micrograph of a patterned sample. Well-defined, alternating lines of graphene (10 µm wide, bright) and bare sapphire (20 µm wide, dark) can still be seen after cell culture.

FIG. 9*d*: Electrical characterization of a graphene solution-gated transistor. The drain-source current is plotted against the gate source voltage and shows a "dip" behavior, which is typical for ambivalent charge transport in graphene. From these measurements, mobilities higher than 8000 $cm^2 V^{-1} s^{-1}$ can be calculated.

FIGS. 10*a* to 10*b* present the pure new-born retinal ganglion cells (p7) cultured on sapphire/graphene patterns.

FIG. 10*a*: Scanning electron microscope image of cell aggregates in the vicinity of the limit between patterned and unpatterned areas, corresponding to the DIC image in FIG. 8*c*. The top square corresponds to the SEM image in FIG. 3*e*.

FIG. 10*b*: SEM image of the cell aggregate marked by the bottom square in (10*a*).

Figure 11:
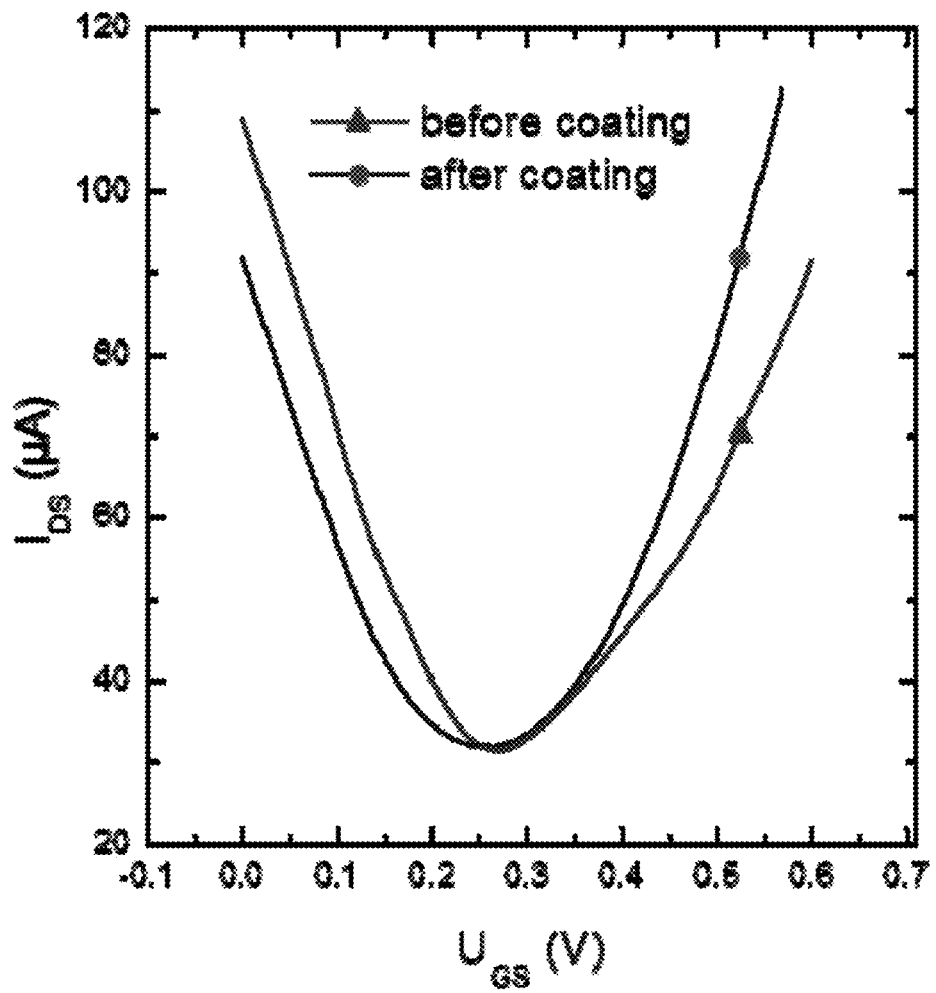

FIG. 11. Influence of the poly-D-lysine/laminin coating on the electronic properties of graphene has been assessed. Graphene solution-gated field effect transistors (SGFETs), fabricated as discussed elsewhere (Dankerl, et al., 2010), were characterized before and after the coating. The transistor characterization was performed in an aqueous electrolyte containing phosphate buffered saline (5 mM) at a pH of 7. For all investigated transistors, an average shift of the Dirac point of −60 mV was observed, which is in agreement with the expected shift induced by the positively charged poly-D-lysine coating. Such a shift approximately corresponds to a charge density of 1012 charges per $cm^2$. Both before and after coating the transistors reach transconductances of 3-4 $mS·V^{-1}$ (normalized by the drain-source voltage). This suggests that the carrier mobility remains unchanged after coating, thus confirming that the poly-D-lysine/laminin coating does not influence the electronic properties of graphene.

Figure 12:
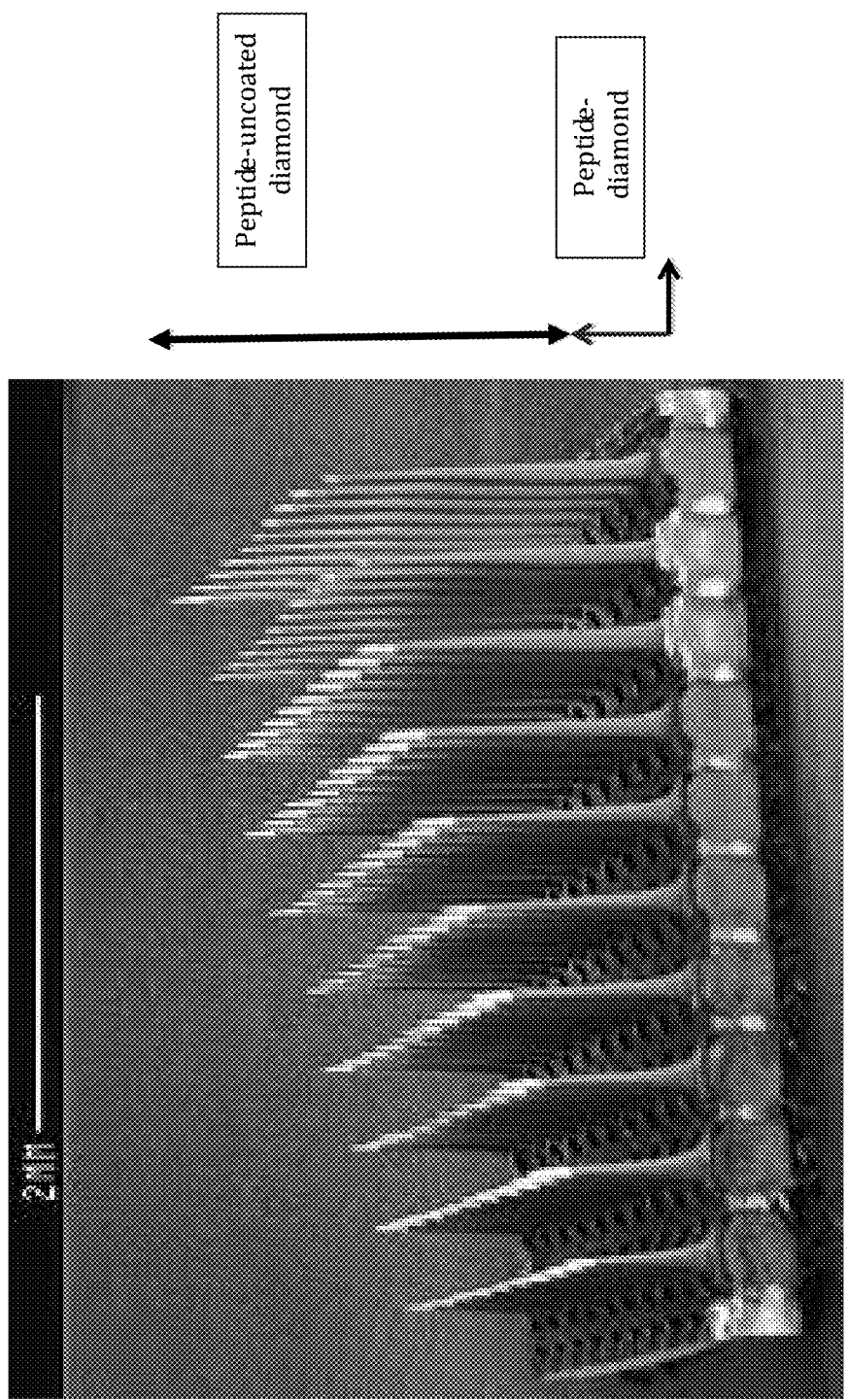

FIG. 12 presents an example of an implant constituted with several electrodes of the invention carbon-based material such as diamond, or graphene.

Up vertical arrow corresponds to the first carbon-based material (non coated) and down vertical arrow corresponds to the second carbon-based material (coated).

The length of each first and second carbon-based material described here is given for example only and the invention is not limited to this length.

First and second carbon-based material constitutes an electrode.

Such electrodes can be put together to constitute an implant or a prosthesis liable to stimulate neurons.

Thus the space between two neighbor electrodes must also be coated.

Figure 13:
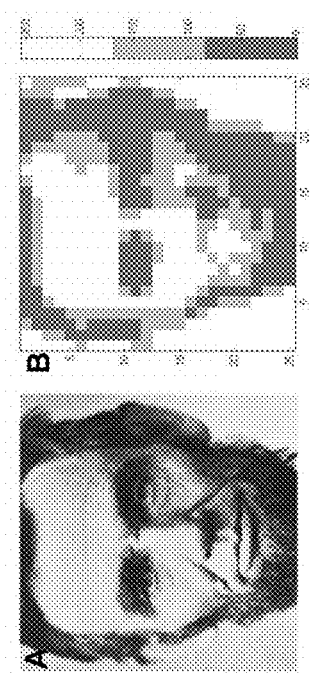

FIG. 13 represents an image of Abraham Lincoln before (A) and after (B) down sampling to 25×25 pixels and reducing color palette to 4 grayscale levels.

Figure 14:
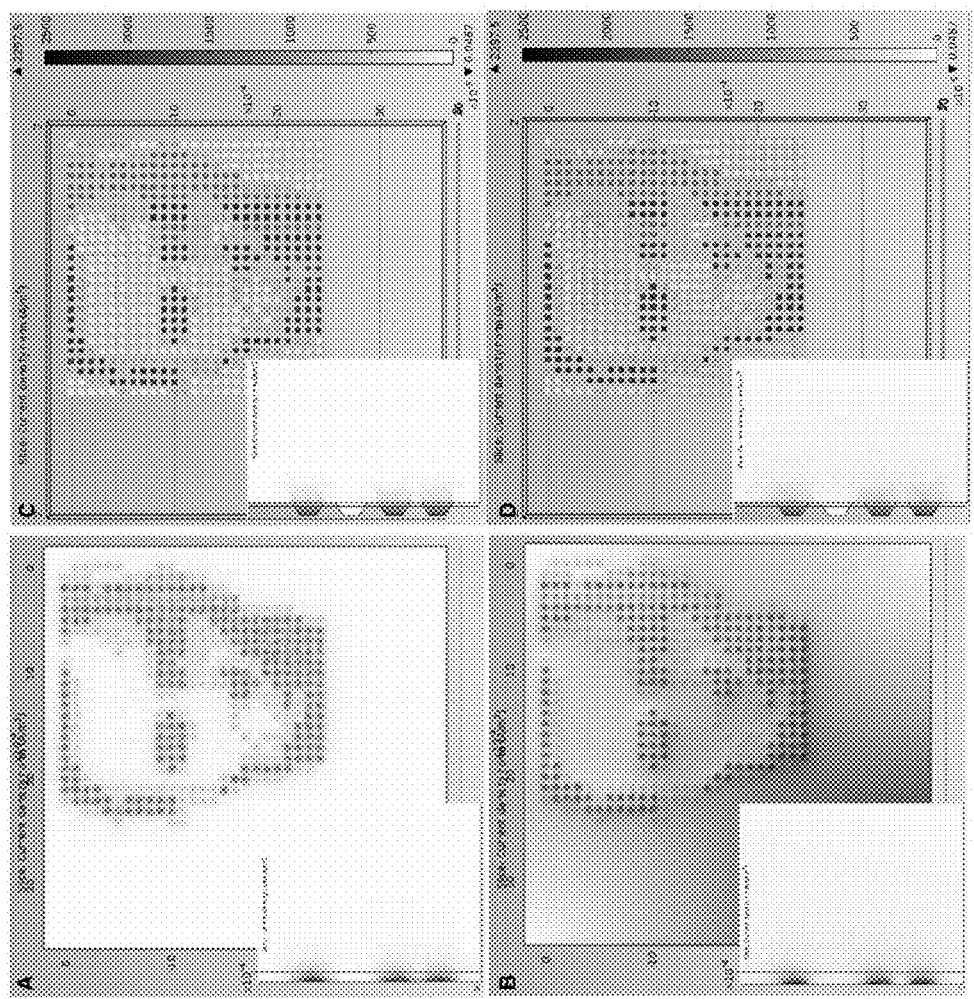

FIG. 14 represents the current density plots 20 μm above the electrode array for the four simulated models, visualized by a red line on each respective slide view.
A: planar with surrounding counter-electrode;
B: planar with distant counter-electrode located in the lower right corner;
C: three-dimensional with the counter-electrode surrounding the wells;
D: three-dimensional with a distant counter-electrode located in the same position as in B.

Figure 15:
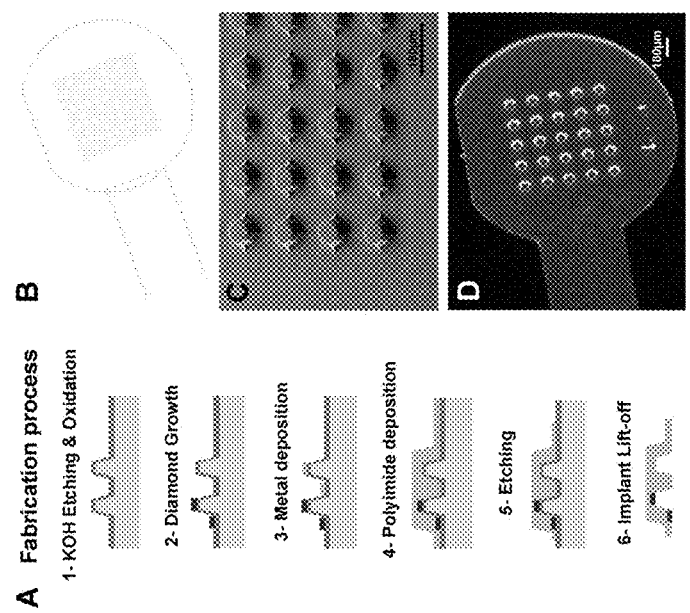

FIG. 15 represents a fabrication of flexible diamond implants. A: schematic of the microfabrication steps; B: Picture of mask (Yellow: KOH structures, Red shape of implant); C: SEM picture of Silicon Mould; D: Final dummy implant for in vivo evaluation.

Figure 16:
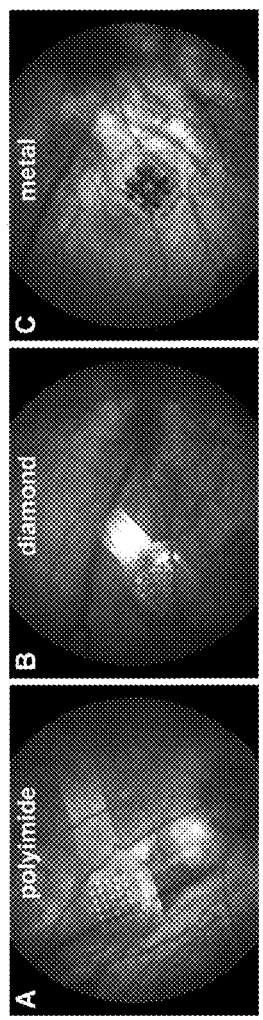

FIG. 16 represents eye fundus of P23H rats implanted with polyimide (A), diamond (B) and metallic (C) devices.

Figure 17:
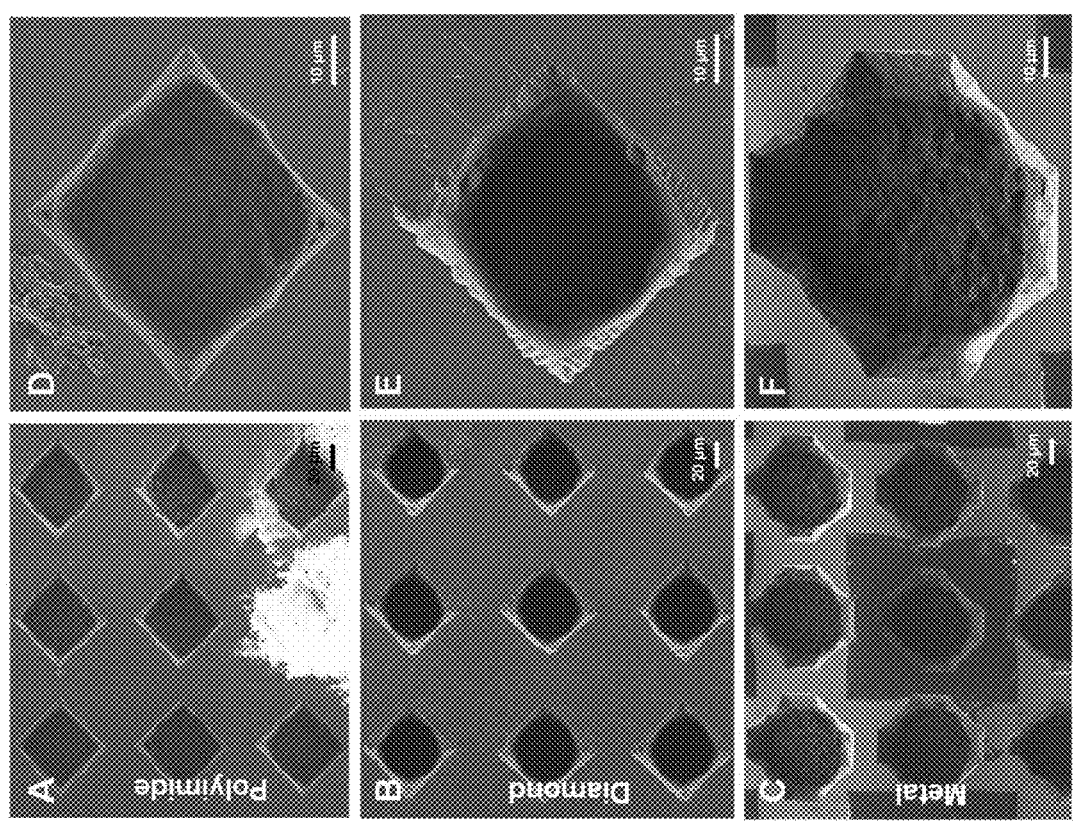

FIG. 17 represents Scanning Electron Micrographs of polyimide (A, D), diamond (B, E) and metal (C, F) implants.

Figure 18:
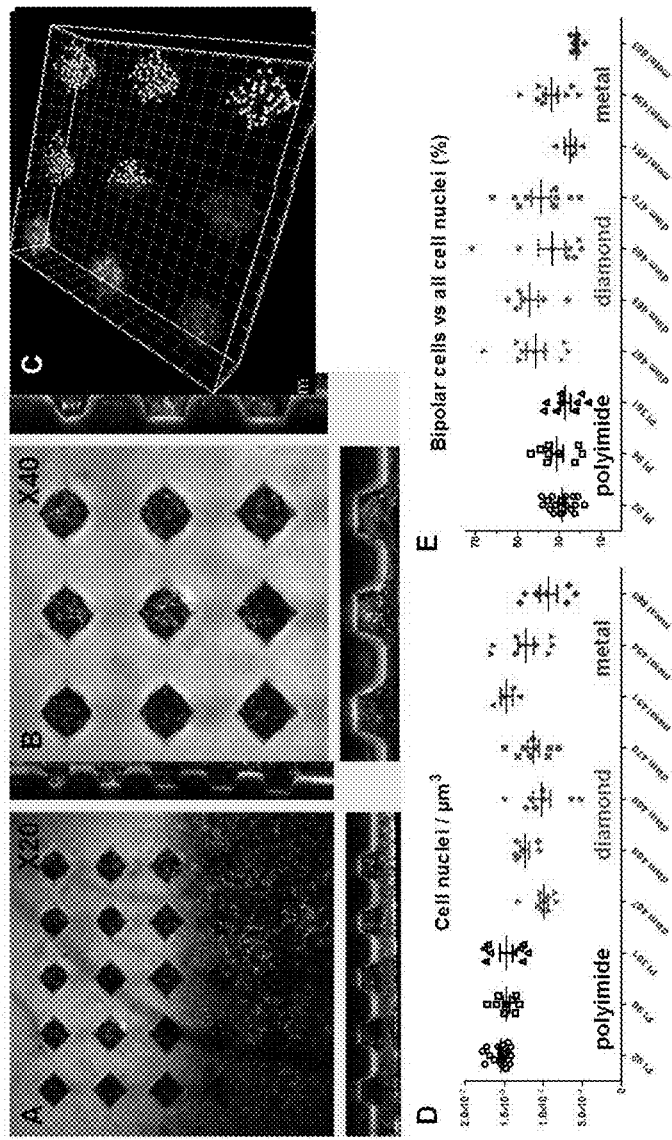

FIG. 18 represents confocal imaging of stained retinae in contact with implant+quantification of bipolar cell within the 3D electrodes for each material.

Figure 19:
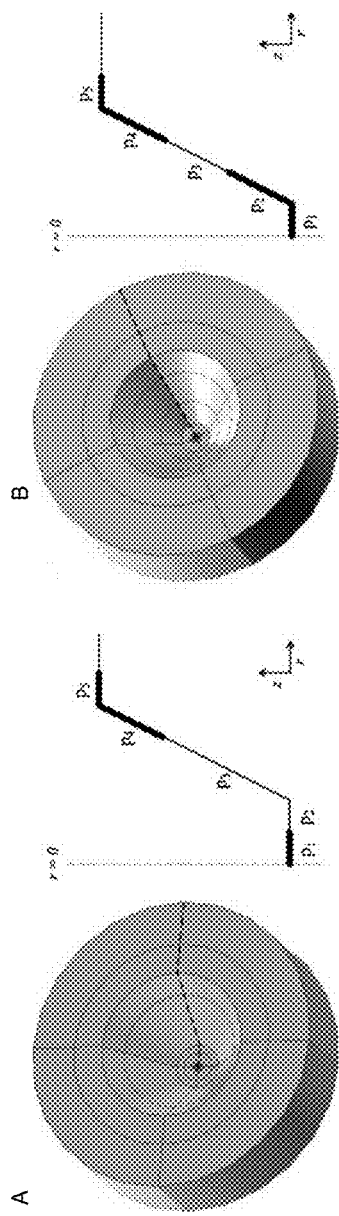

FIGS. 19 (A) and (B) (from Djilas et al., 2011) represent 3D electrode geometries and their corresponding half cross sections. The dashed lines in the 3D representations mark geometry half cross sections. Each electrode half cross section is defined with five parameters (p1-p5) which represent the lengths of the segments.

Cavity wall inclination is 54.7° for both geometries. Active electrode segments (thick lines in the half cross sections) are separated by insulated segments (thin lines in the half cross sections).

EXAMPLES

Example 1: Diamond Material

Example 1-1: Diamond Growth and Samples Preparation

Nano-crystalline diamond films were produced on Corning incorporated Glass 1737-F (6×6×1 mm$^3$). On these glass plates, detonation diamond nano-particles (6-nm) dispersed in water (0.1% wg) were spread by spin coating. Then a 300 nm-thick nano-crystalline diamond film was grown at low temperature in a SEKI TECHNOTRON CORP AX6500 Microwave Plasma Chemical Vapor Deposition (MPCVD) system. The growth parameters are provided in Table 1. Then, these Hydrogen-terminated diamond surfaces were oxidized by immersion during 30 min in a boiling solution containing 98% concentrated sulphuric acid and an excess of potassium nitrate ($H_2SO_4$/$KNO_3$). Diamond on glass substrates were reused by exposing them to a hydrogen plasma treatment. This treatment was achieved in the same reactor that was used for diamond growth but in the condition described in Table 2. For the current study, after growth the samples were cut in 6×6 mm$^2$ chips in order to provide biologists with statistically representative series of samples (typically 100) for the performing of cell culture studies. Hydrogen-terminated diamonds were stored in a sterile petri dish just out of the reactor and were rinsed with sterile culture medium right before seeding the cells on them.

TABLE 1

Diamond growth conditions on glass substrates

| MW power (kW) | Pressure (mbar) | H$_2$ flow (sccm) | CH$_4$ flow (sccm) | Temperature (° C.) | Duration (h) |
|---|---|---|---|---|---|
| 2 | 30 | 196 | 4 | 650 | 4 |

TABLE 2

Diamond hydrogenation conditions

| MW power (kW) | Pressure (mbar) | H$_2$ flow (sccm) | Temperature (° C.) | Duration (h) |
|---|---|---|---|---|
| 1.7 | 35 | 200 | 650 | 0.5 |

Example 1-2: Micro-Contact Printing of Peptide Patterns

Microstamps were produced by photolithography and molding (Mrksich et al., 1997; Chang J C, 2001). An electron beam writer transposed the gradient structures into a chrome mask. Applying UV-photolithography, master stamps were produced using 5-12.5 μm thick positive photoresist (AZ 5206) layers on 0.6 mm thick silicon wafers. Pattern transfer was achieved by deep reactive ion etching (2.5 μm deep). Finally, the mold was passivated by covalently linking a (trichloro (1H, 1H, 2H, 2H-perfluorooctyl) silane layer to its surface in a vapor deposition (Mrksich et al., 1997) process to support an easy release of the plastomer and reuse of the mold. Poly(dimethylsiloxane) (PDMS) microstamps were fabricated curing Sylgard 184 (Dow Corning, Midland, USA) onto these masters followed by curing at 55° C. for 48 h. After master stamp release, final curing was performed for 1 h at 110° C. Inking took place by immersing the stamp for 20 min in 10 μg/ml FITC-(fluorescein isothiocyanate) conjugated poly-L-lysine (FITC-PLL) (Sigma, Germany) mixed with 2 μg/ml laminin (from mouse sarcoma, Sigma L2020) both diluted in Hank's Balance Salt Solution (HBSS). The stamp was dried in nitrogen stream and pressed for 2 minutes onto the diamond substrate, pre-sterilized with 70% ethanol pA.

Example 1-3: Analysis of the NCD Thin Films: Ellipsometry and XPS Measurements Ellipsometry and XPS measurements were used to characterize oxidized and hydrogenated diamond substrates with or without a peptide coating. As hydrogen termination is altered by natural diamond oxidation in air, surface hydrogenation was performed just prior to the ellipsometry characterization in a semi-industrial Microwave Plasma Chemical Vapour Deposition (MPCVD) reactor SEKI AX6500. The experimental conditions were: microwave power 2200 W, pressure 25 mbar, hydrogen flow 200 SCCM and temperature 650° C.

A UV-Vis Spectroscopic Ellipsometer (Horiba Jobin-Yvon, UVISEL), at a fixed angle of 70°, was used to characterize the roughness and the thickness of diamond films. For both oxidized and hydrogenated surfaces, the diamond sample was fixed onto the ellipsometer in order to always characterize the same area. Measures were obtained on the "bare" surface 3 times, and then a 20 μl drop of either deionized water or 0.1 mg/ml of poly-D-Lysine in water was deposited onto the sample. After 45 min at room temperature, the sample was thoroughly rinsed with deionized water and dried with argon. Finally, measures were taken 3 more times on the same area but on the "coated" sample. The use of a three-layer micro-structural model is necessary to obtain a good fit of the experimental data (surface roughness/diamond/silicon) (Lions et al., 2009). Towards the modelling of the optical constants, they were fitted using a Tauc-Laurentz dispersion law (Gupta et al., 2008). For both "bare" and "coated" samples, the same model was used: diamond thickness and apparent diamond thickness were extracted, respectively. A plot of the difference in apparent diamond thickness once the surface is coated with respect to before the coating was then realised.

Surface analysis was also performed by X-ray photoelectron spectroscopy (XPS) onto those samples. The spectrometer anode supplied was provided with a hemispherical analyser and an Al—K monochromator. Binding energies were referenced to the $Au4f_{7/2}$ peak located at 83.6 eV. A curve fitting procedure was carried out on smoothed spectra to extract the components in the N1s spectrum using Voigt functions with a Lorentzian half-width of 0.2 eV and 0.6 eV, respectively.

Example 1-4: Animals

Long-Evans rats, used for cell cultures, were purchased from Janvier (Le Genest Saint-Isle, France). All Experiments have been carried out in accordance with the European Community Council Directives (86/609/EEC) and with the ARVO (Association for Research in Vision and Ophthalmology) statement for the Use of animals in ophthalmic and visual Research.

Example 1-5: Primary Retinal Cell Cultures

Mixed Retinal Cells

Primary mixed cultures of retinal cells were isolated from retinae of adult Long Evans rats (8 week-old). Animals were anesthetized and sacrificed; their eyes enucleated and placed in a solution of $CO_2$-independent medium (Life Technologies, Carlsbad, Calif., USA). Retinae were cut in pieces of about 2 mm$^2$ and rinsed twice in Ringer medium. Retinal pieces were then incubated for 25 min at 37° C. in a solution of 2 UI/ml of papain (Worthington, Lakewood, N.J., USA), previously activated for 30 min at 37° C. in Ringer medium. They were then rinsed with Neurobasal-A medium (Life Technologies, Carlsbad, Calif., USA) containing 10% of Foetal Bovine Serum (FBS; Sigma) and 2.5% of DNAse (DNAse, Sigma). Retinae were dissociated in this latter medium, in four steps, using 1 ml cones and adding 1 ml of the solution of Neurobasal-A medium and 10% FBS at each step. Cell suspension was centrifuged at 115 g during 6 min at room temperature. Supernatant were removed and the pellet was resuspended in Neurobasal-A medium (Life Technologies), which contained 2 mM L-glutamine (Life Technologies) and 2% of B27 (Life Technologies). Finally, cells were counted by addition of 10% of trypan blue (Life Technologies) using a malassez hemocytometer. They were seeded in the same medium (NBA+) at an initial density of $2\times10^4$ cells/cm$^2$ on 8 mm-diameter glass coverslips or on 6×6 mm$^2$ diamond samples, either coated by successively poly-D-lysine (2 μg/cm$^2$ for 45 min; Sigma-Aldrich) and laminin (1 μg/cm$^2$ overnight; Sigma-Aldrich) or uncoated.
NBA=Neurobasal medium.
NBA+=NBA with 2% B27 and 1% de Glutamine.
The composition of B27 is described below:
Biotine Selenium
L-carnitine T3 (triodo-1-thyronine)
Corticosterone DL-α-tocopherol (Vitamin E)
Ethanolamine DL-α-tocopherol acetate
D (+)-galactose Proteins
Glutathione (reduced) Albumin bovine
Linoleic acid Insuline
Linolenic acid Catalase
Progesterone Superoxide dimutase
Putrescine Transferrin
Retinyl acetate
Pure Retinal Ganglion Cells (RGCs)

RGCs were isolated from retinae of adult Long-Evans rats (8-week old) with an immunopanning technique, according to protocols previously described in young rats (Barnes et al., 1988) and adult animals (Fuchs et al., 2005a). As well as for the mixed cultures, cells were seeded at an initial density of $2\times10^4$ cells/cm$^2$ on glass coverslips and diamond samples, with or without peptide coating on the whole surface or as a pattern.

Example 1-6: Viability Test

Cell viability was assessed with the "lived-dead" test (Life Technologies), which consists in labelling viable cells with calceinAM detected as green fluorescence, whereas dead cells were labeled with ethidium Iodide producing a red fluorescence. Briefly, coverslips were incubated in a mixture of calceinAM and ethidium homodimer-1 (diluted in a PBS medium) for one hour in the incubator (humidified chamber, 37° C., 5% $CO_2$). Only alive RGCs were counted from seven fields selected identically on each coverslip using a microscope (Leica DM 5000B, Solms, Germany) equipped for epifluorescence. Viable RGCs were counted at 1 and 6 days in vitro (DIV). When evaluating the effect of the different materials, the results were presented as a percentage of cell survival at 6 DIV with respect to 1 DIV.

Example 1-7: Immunocytochemistry and Fluorescent Imaging

Cell cultures were fixed with 4% paraformaldehyde (Sigma) in PBS (Sigma) for 15 min at room temperature (20° C.). Cell cultures were rinsed, permeabilized for 10 min in PBS containing 0.1% Triton X100 (Sigma) and pretreated with PBS containing 3% BSA (Sigma), 10% normal goat serum (Sigma-Aldrich) and 0.1% Triton X100 for 1 h to reduce non-specific labelling. Primary antibodies were applied on the cell cultures for 2 h at room temperature (anti-G0α diluted at 1/1000 for bipolar cells staining and anti-GFAP diluted at 1/500 for glial cells staining). After several washes, cell cultures were incubated with a goat anti-rabbit IgG antibody conjugated to Alexa™ 488 (Molecular Probes, Eugene, Oreg., USA) and Alexa™ 594 (Molecular Probes, Eugene, Oreg., USA) diluted at 1/500 for 1 h at room temperature. Nuclear labelling was achieved by incubating the cell cultures in a DAPI solution with the secondary antibody. Cell cultures were rinsed four times with PBS-Triton 0.1%, once with PBS only and at last once with distilled water before mounting. The fluorescent labelling was observed using a Leica DM 5000 microscope with epifluorescence illumination (Alexa™ 488: excitation filter 480±40 nm; Alexa™ 594: excitation filter 560±40 nm).

Example 1-8: Quantification: Cell Viability, Neurite Sprouting and Colocalization Density of pure cultured RGCs was evaluated by counting calceinAM-positive viable cells at 6 days in vitro (DIV) from seven fields selected identically on each coverslip under an epifluorescence microscope (Leica DM 5000B). Full glass coverslips and diamond samples were digitalized (~300 fields for a 10× magnification) to automatically quantify (i) the neurite sprouting for the pure RGC cultures and (ii) the colocalization of cells and neurites on the protein patterns using MetaMorph software (Ropper scientific). The <<Neurite Outgrowth>> application takes into account the diameter of the cell bodies, the width of the neurites and their intensities above background.

For the cell colocalization with the patterns, images of the different microscope fields were thresholded and the colocalized area of both images (cells and pattern) was expressed as percentages.

For the mixed cultures, glial cell area was measured with Metamorph software using an automatic threshold on the image, quantifying only the area stained with GFAP.

Example 1-9: Statistical Analysis

All data are expressed as means±s.e.m. One-way ANOVA was used for variance analysis, followed in case of significance by either a Bonferroni post-hoc test (Gaussian distribution) or a Dunns post-hoc test (no Gaussian distribution) to compare the means of each group. Differences were considered significant at *$p<0.05$, $p<0.01$ and *$p<0.001$.

Conclusion:

The present study further confirms that neuronal tissue cells can be grown on diamond. Here it has been demonstrated that pure adult retinal neurones can survive on uncoated diamond whereas glial cells prefer peptide coated diamond. Pure neurones even generate longer neurites on bare diamond than on peptide coated diamond. When both grounds are present, these neurites do not select the peptide-coated diamond much more significantly than the bare diamond by contrast to peptide-coated glass versus bare glass. These results therefore highlight some hints on the diamond use in neuroprostheses.

Diamond Biocompatibility on Neuronal Tissue Cells

Two studies had investigated this point with cultures of embryonic cortical neuronal cells (Specht et al., 2004; Thalhammer et al., 2010). In these studies, diamond layers (polished polycrystalline or nanocrystalline) appeared to provide a substrate equivalent to glass for neuronal growth. Indeed, they all allowed neuronal growth only when peptide coated or covered with dispersed nanodiamond particle. In these studies, neurons were mixed with glial cells and both cell types were not surviving directly on the uncoated polished polycrystalline or nanocrystalline diamond layers. However, as neuronal survival was often reported to rely on glial cell presence or addition of glial-conditioned medium (Fuchs et al., 2005b), it remained unclear whether the poor neuronal survival on uncoated diamond was specific or indirectly related to the absence of glial cell growth.

Similarly no major difference between glass and diamond for the survival of mixed retinal cells was found in the invention. By contrast to these studies, both glial cells and bipolar neuronal cells on uncoated nanocrystalline diamond layers as on uncoated glass were observed.

When counting glial cells and bipolar cell neurones, the decrease in glial cells was greater than that of neurons on the uncoated diamond layers. These results suggested that glial cells are more sensitive to culture substrates than neurons. The square shapes of glial cells on the patterned substrates with processes elongating along the linear peptide coating further confirmed their strong preference for the peptide coating. Therefore, when glial cell adhesion to the material is required, peptide coating of diamond layers should be strongly recommended. For such a peptide coating on the diamond surface, H-terminated diamond have to be preferred because the peptide coating is thicker on these substrates with respect to O-terminated diamond as indicated by surface state measurements.

Dispersed nanodiamond particles appear as an alternative to peptide coating because embryonic neuronal cultures survived very well on these particles (Thalhammer et al., 2010). In fact, it would be difficult to consider solely these particles for implant coating because they are not bound to the substrates and could therefore be engulfed and moved to other tissues by phagocytes. However, the growth of embryonic neuronal cultures on these dispersed nanodiamond particles (Thalhammer et al., 2010) suggests that chemical or physical modifications of diamond surfaces occurring during the particle preparation can change cellular interactions with glial cells. Further studies will therefore have to investigate how chemical and physical modifications of diamond can modify glial cell adherence and growth.

By contrast to previous studies using embryonic cell cultures (Specht et al., 2004; Thalhammer et al., 2010), adult neurons surviving directly on the diamond substrates were often observed indicating that they do not require peptide coating at the interface with diamond or glass. However, in these mixed cultures, neurons were less dense on diamond and glass than on the peptide coated substrates. This decrease in the number of surviving neurons could in fact result from the decrease in glial cell number because glial cells are known to release important factors for neuronal survival (Fuchs et al., 2005b). To eliminate this glial variable, neuronal survival was assessed using pure retinal neurons following the purification of adult retinal ganglion cells. This preparation showed that the peptide coating did not influence neuronal cell survival and even suppressed neurite outgrowth on both glass and diamond. These observations suggest that a direct neuron/diamond interface is compatible with neuronal cell survival and neurite development. Such a direct interface could be very important to increase stimulation yields in neuroprostheses. Although neuronal processes were longer on uncoated glass, they preferred to grow on the peptide-coated glass when both grounds are available. Using embryonic neuronal cell cultures, neuronal cell processes were similarly reported to grow preferentially on the peptide-coated diamond substrates (Specht et al., 2004). In our hands, this strict preference for the peptide-coated diamond substrates was not recovered when using pure adult retinal ganglion cells. This result confirmed further that adult neurons can well survive and grow neurites directly on diamond.

Diamond in Neuroprostheses

For neuronal stimulation, the tissue/implant interface has to be as tight as possible to limit ionic diffusion at the surface of the implant, which would limit the resolution of individual electrodes and the current intensity to be injected for reaching the activation threshold of the neurons. In fact, neuronal tissues are always surrounded by a glial cell layer acting as a physical barrier. Therefore, neuroprostheses can either be deposited on this glial surface or exhibit penetrating electrode invading into the neuronal tissue. For surface implants, it will be important therefore to increase the glial cell adherence to the implant and electrodes. Therefore when considering the use of diamond electrodes, these results suggest that peptide coated diamond has to be selected. This applies particularly for retinal implants, which will come in direct contact to the inner limiting membrane (epi-retinal implants) or the outer limiting membrane (subretinal implant) both formed by glial Müller cells. The outer limiting membrane is indeed covering the retina on the photoreceptor side after the loss of photoreceptor inner and outer segments.

In case of penetrating implants, a massive glial response was found to develop around electrodes within a few months (Maynard et al., 2000). This massive gliosis may explain the loss of electrical stimulation occurring in a few months after implantation as in cortical prostheses. This massive gliosis is likely to occur to reconstitute the continuity in the external glial barrier preventing any tissue change in ionic homeostasis. This suggests that holes created by the penetrating needles or electrodes should be rapidly sealed. The sealing of these holes could be achieved by applying a molecule promoting glial cell adhesion at the basis of penetrating needles or on the implant socket. This material could be for instance any peptide-coated material like peptide coated diamond. An adequate sealing at the basis of the electrode may prevent further gliosis around the needle tips where stimulating electrodes are displaced. In fact, direct contact or close distance between neurons and electrodes is expected to provide the best electrical stimulation with the minimum current intensities. Therefore, our results suggest that bare diamond without any peptide coating should be used at the needle tips where stimulating electrodes are located to limit glial cell adherence and growth but favor instead direct contacts to neuronal processes.

Conclusion

This study confirms the biocompatibility of diamond for neurones and glial cells. It therefore strengthens the need to consider diamond as an attractive electrode material for applications with stimulation of the neural tissues is sought.

Example 2: Graphene Material

Example 2-1: Graphene Preparation and Processing

Graphene Growth and Transfer.

Single layer graphene was prepared by chemical vapor deposition (CVD). After an annealing of the copper foil at 1000° C. under hydrogen flow (35 sccm) for 15 min, the gas composition was changed to a hydrogen/methane mixture (10 sccm/35 sccm) and the graphene was grown on copper foil at 1000° C. for 30 min. As reported previously [Li, et al., 2009], a high surface coverage of single layer graphene is obtained under these conditions [Hess, et al., 2011]. For the wet transfer of graphene to sapphire, the copper/graphene films were covered with a poly(methyl 2-methylpropenoate) (PMMA) layer for transfer. This stack was placed on a $FeCl_3$ solution (0.5M) to etch the copper. Afterwards, the graphene/PMMA film was transferred to sapphire substrates and the PMMA was stripped with solvents. Finally, samples were annealed in UHV in order to reduce surface contamination.

Linear Patterns of Graphene on Sapphire Substrates.

10 µm-wide graphene lines were patterned on the sapphire substrates by using UV-photolithography and a subsequent oxygen plasma treatment.

Example 2-2: Primary Retinal Cell Cultures: Purification of Retinal Ganglion Cells (RGCs)

Cell cultures were prepared from Long-Evans rats, which were purchased from Janvier (Le Genest Saint-Isle, France). All Experiments have been carried out in accordance with the European Community Council Directives (86/609/EEC) and with the ARVO (Association for Research in Vision and Ophthalmology) statement for the *Use of animals in ophthalmic and visual Research.*

RGCs were isolated from retinae of adult and new-born Long-Evans rat (8-week old and postnatal day 7), with an immunopanning technique, according to protocols previously described in young rats [Barres, et al., 1988] and adult animals [Fuchs, et al., 2005b]. Cells were seeded at an initial density of $2 \times 10^4$ cells·cm$^{-2}$ on glass coverslips, graphene and sapphire samples, in Neurobasal-A medium (Life Technologies), which contained L-glutamine (2 mM, Life Technologies) and B27 (2%, Life Technologies) for adult cells and ND-G medium [Barres, et al., 1988] for new-born, either coated by successively poly-D-lysine (2 µg·cm$^{-2}$ for 45 min; Sigma-Aldrich) and laminin (1 µg·cm$^{-2}$ overnight; Sigma-Aldrich) or uncoated. The poly-D-lysine/laminin coating does not influence the electronic properties of graphene, as discussed in the Supporting information.

Example 2-3: Viability Tests

Cell viability was assessed with the "lived-dead" test (Life Technologies), which consists of labelling viable cells with calceinAM detected as green fluorescence, whereas dead cells were labeled with ethidium Iodide producing a red fluorescence. In each experiment, both the coated and the uncoated conditions included two glass plates, three graphene and three sapphire substrates. After 6 days in culture, they were incubated in a mixture of calceinAM and ethidium homodimer-1 (diluted in a PBS medium) for one hour in the incubator (humidified chamber, 37° C., 5% $CO_2$). Digital images of calceinAM-positive viable cells (630 µm×750 µm) were obtained at 15 fixed independent locations under an epifluorescence microscope using a 10× objective (Leica DM 5000B, Solms, Germany). The numbers of viable RGCs were normalized in each experiment to those surviving at 1 day in vitro (DIV) on peptide-coated glass. All quantifications (cell numbers, cell sizes, neurite lengths, process number) were all obtained automatically from the digital images using the specific applications of Metamorph (Ropper scientific). Each experiment was then repeated at four times with all the substrates with or without coating.

Example 2-4: Mixed (Adult) Retinal Culture on Graphene and Glass Fixed at 6 Days In Vitro The method used is as in Example 1.5

Results are presented in FIGS. 5A to 5H.

Example 2-5: Statistical Analysis

All data are expressed as means±s.e.m. Two-way ANOVA test was used for variance analysis, followed in case of significance by either a Bonferroni post-hoc test to compare the means of each group. Differences were considered significant at *p<0.05, p<0.01 and *p<0.001.

Figure 6:
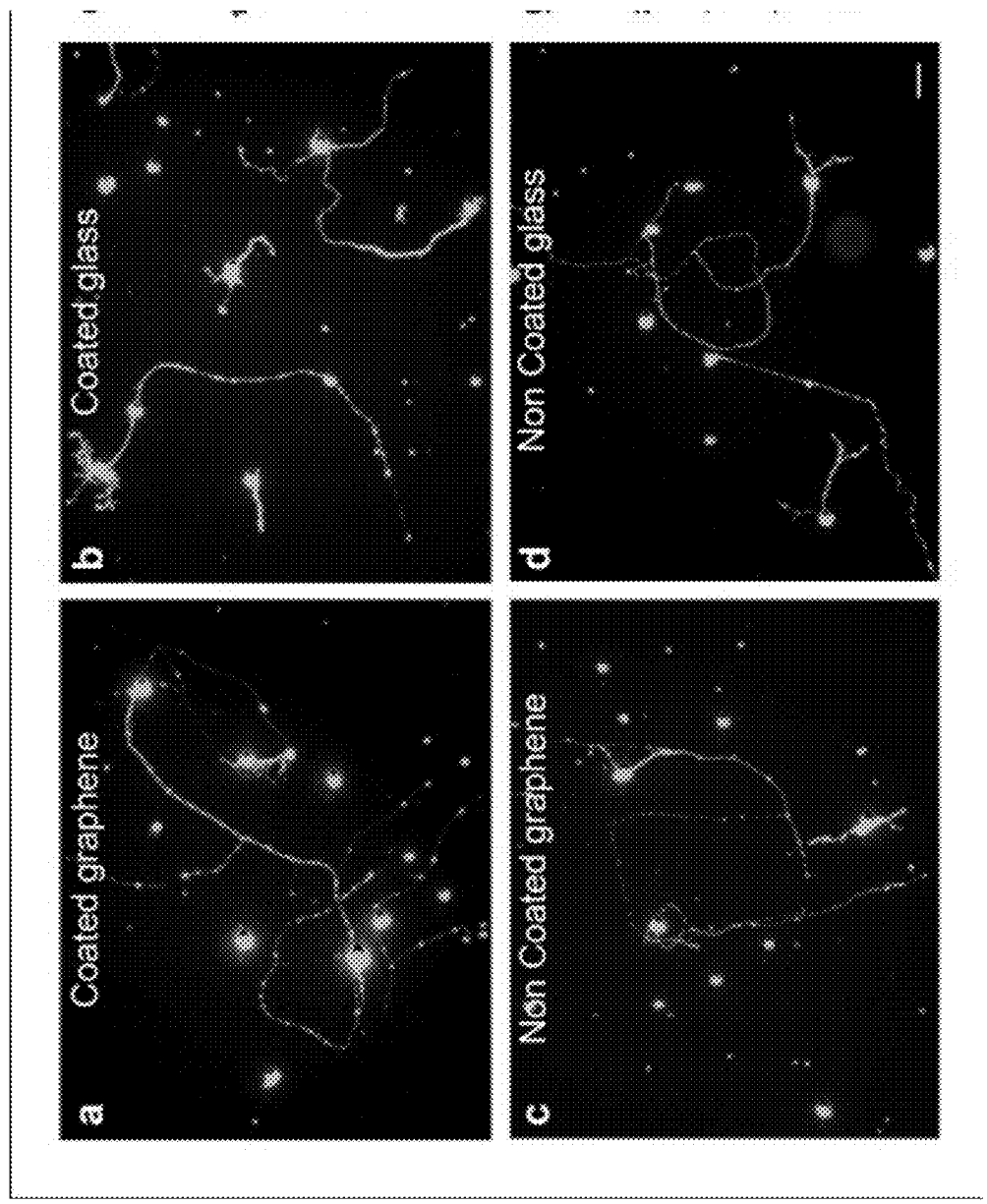
Figure 6:
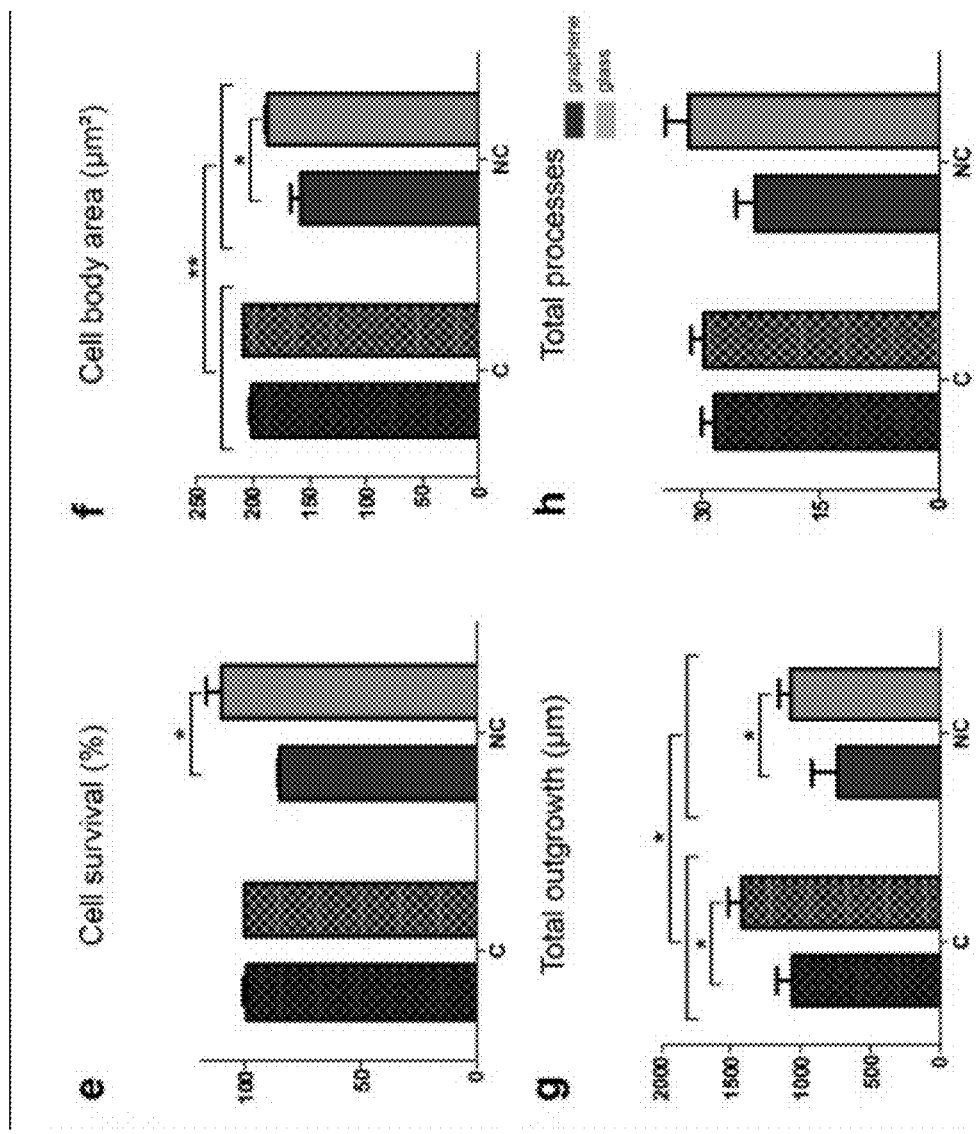

Conclusion:

FIG. 6 illustrates the viability of adult retinal neurons after 6 days in vitro, not only on peptide-coated graphene but also directly on bare graphene. All viable neurons exhibit neurite outgrowth on any substrate, peptide-coated or uncoated (FIG. 6*a-d*). The survival rate was quantified in repeated experiments and no statistically significant differences were observed between peptide-coated substrates, either glass or graphene. Surprisingly, the peptide coating did not increase the survival rate on glass in contradiction to common views for cell cultures [Clark, et al., 1997; Fricke, et al., 2011]. On bare graphene, on the other hand, viable cells were slightly less numerous than on glass or peptide-coated substrates; such differences, even if small, are statistically significant (see FIG. 6e). However, despite this slight decrease in cell number on bare graphene, the presence of neurons with outgrown neurites on this bare substrate strongly confirms the high cytocompatibility of graphene. To further investigate any difference between glass and graphene substrates, several parameters including cell size and neurite outgrowth on the different substrates were quantified. When peptide-coated, glass and graphene offered no difference. However, in the absence of coating the cell size was smaller on graphene than on glass suggesting thereby that cells had more difficulty to adhere and to spread over bare graphene (FIG. 6f). This difference in cell adherence could also explain why neurite lengths were significantly reduced on bare graphene as compared to all other substrates (FIG. 6g). In addition, it could provide an interpretation for the apparent reduction in the process number even if the difference was not statistically significant (FIG. 6h). These observations indicate that adult neurons can nicely survive and grow neurites directly in contact with bare (i.e. non peptide-coated) graphene.

To further assess neurite sprouting on graphene as well as on graphene patterns, postnatal retinal ganglion cells (postnatal day 7) maintained in a Neurobasal-based medium (containing growth factors, hormones and vitamins were used [Barres, et al., 1988]. The developmental stage of postnatal cells makes them particularly prone to such outgrowth [Adler, et al., 1990]. To investigate the effect of graphene patterns on cell growth, we also evaluated sapphire since it is used as a substrate to deposit graphene. The numerous cell bodies and the very high densities of cell processes observed on all substrates after 3 days (FIG. 7a-f) are consistent with the above-discussed graphene cytocompatibility for adult neurons.

Figure 7:
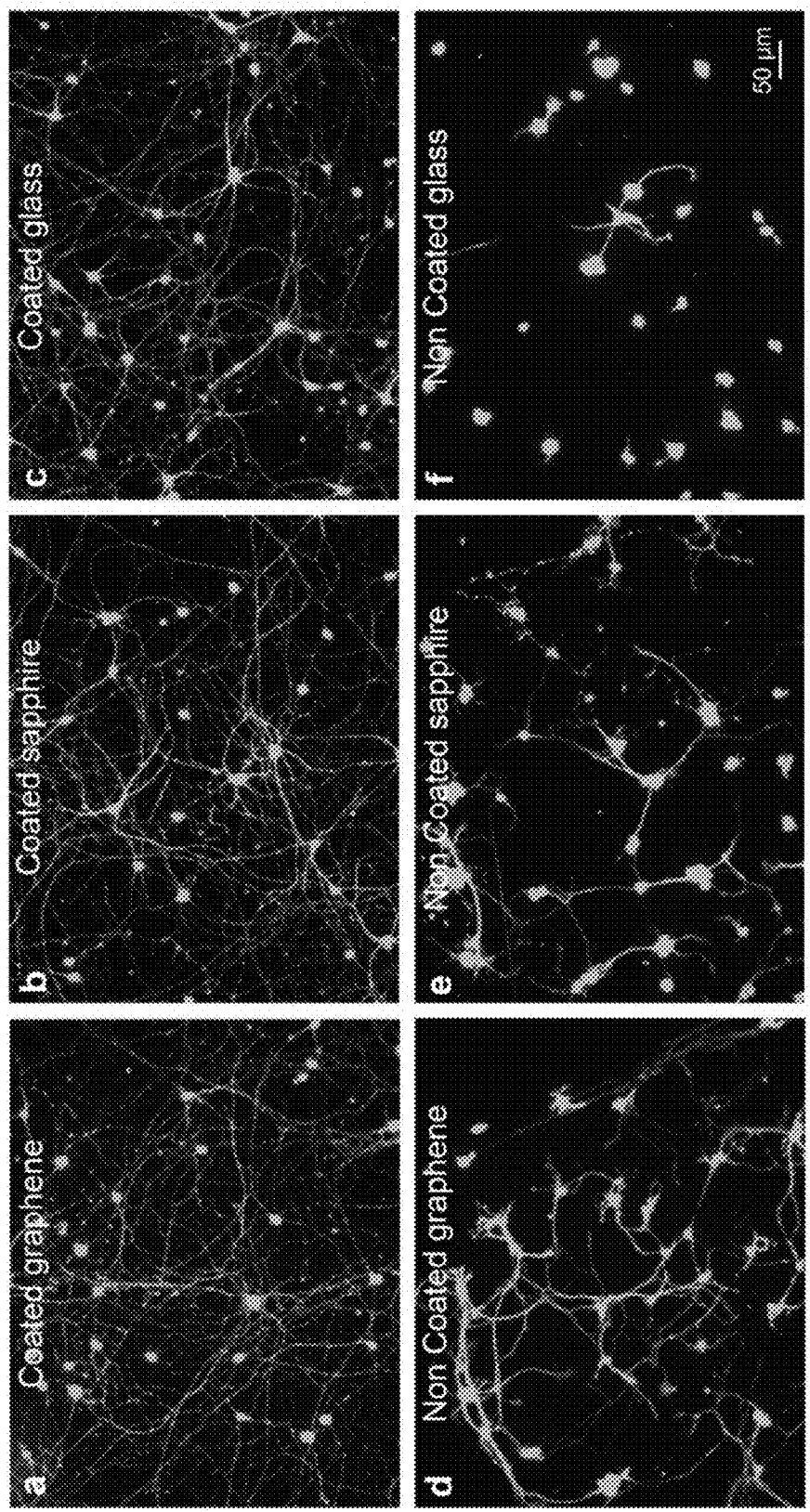
Figure 7:
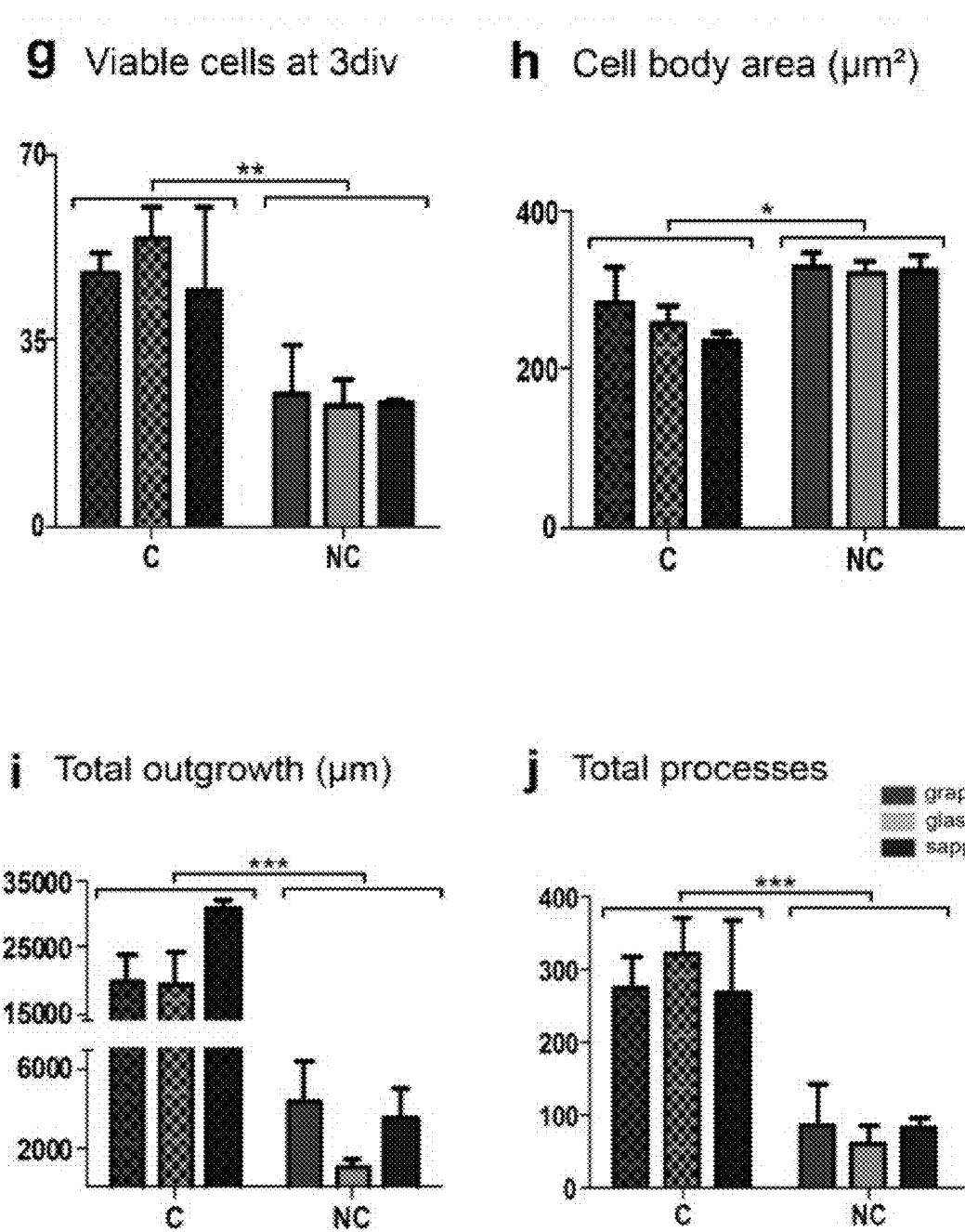

However, the peptide coating of the substrates was found to result in a 2 fold increase of the apparent cell number (FIG. 7g) and a 10 fold increase of the apparent neurite length (FIG. 7i). In fact, the cell morphology was different on bare substrates with an apparent increase in cell body size (FIG. 7h), which is indicative of cell aggregation. Thus, the apparent reduction in cell number for uncoated substrates (FIG. 7g) is partially influenced by this cell aggregation in cell clumps. Furthermore, cell processes on uncoated graphene and sapphire were thicker suggesting the production of neurite bundles [Watkins, et al., 2008] which thus leads to the major reduction in the apparent neurite length (FIG. 7i). This study indicates that young neurons and their neurites have a tendency to aggregate on bare substrates. The peptide coating may therefore improve cell adherence of cell bodies, neurites and their growth cones, such that in its absence all these structures tend to regroup.

Figure 8:
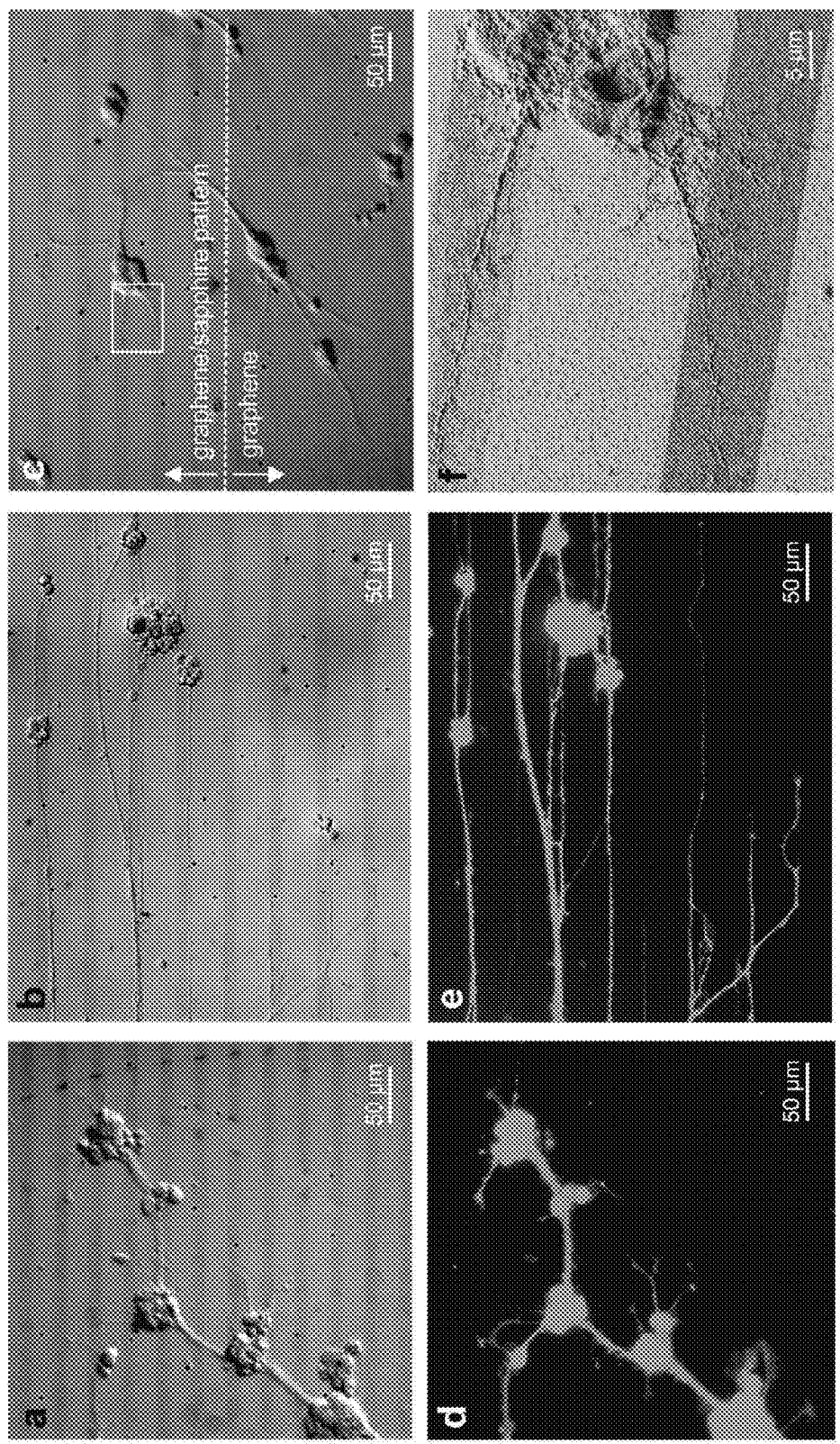

To investigate further the potential competitive advantage of bare graphene as a substrate, postnatal retinal ganglion cells were grown on alternating linear patterns of sapphire (20 or 30 µm-wide) and graphene on sapphire (10 µm-wide) (FIG. 8). No peptide coating was applied prior to the cell culture in order to avoid its potential masking effect of the substrate. Cell morphologies were precisely revealed by the fluorescent live/dead assay while differential interference contrast microscopy was used to localize the graphene patterns. As described above, the cell bodies aggregate to form cell clumps. Similarly, large neurite bundles were seen to emerge from these cell clumps. FIG. 8 illustrates different situations of neurite outgrowth on the graphene patterns. Interestingly, the neurite bundles often follow the edge of the graphene patterns crossing over the lines from time to time. In some occasions, the cell neurites appear to wander independently of the pattern (FIG. 8a). In other cases, however, the neurite sprouting follows very strictly the lines and could cross them (FIG. 8b). FIG. 8e nicely shows an aggregate of 3 cell bodies adhering both on graphene and sapphire while 2 neurites developing from this aggregate grow along neighboring graphene lines, which is confirmed by the corresponding SEM image shown in FIG. 8e (see also FIG. 10). The often observed guidance of neurites at the graphene edge (FIG. 8b) might be due to its chemical composition rather than the physical step, which height is of the order of 1 nm. Due to the technology employed to prepare the graphene/sapphire pattern, the graphene edge is very likely to be decorated with oxygen groups, whereas far away from the edge, no such groups are expected. Such hydrophilic surface has been shown to improve neuronal viability, possibly through improved cell adhesion [Jung, et al., 2001, Liu, et al., 2006, Khan, and Newaz, 2010].

Previous studies have investigated the survival of mixed glial/neuronal cells on polylysine-coated graphene [Li, et al, 2011] or proliferating neuronal cells (stem cells, PC12 cell line) either on laminin-coated graphene or incubated with graphitic nanomaterials (graphene layers) [Park, et al., 2011, Zhang, et al., 2010, Yen, et al., 2011]. The originality of this work lies in the use of purified adult and/or differentiated retinal neurons. In addition, the survival of these neurons was assessed on graphene directly without any peptide coating of the substrate. The importance of the peptide-coating on similar or identical carbon-based materials was even demonstrated using patterns of peptide coating, which allowed embryonic cortical neurons to grow preferentially on the laminin coating rather than directly on the diamond [Specht, et al., 2004]. For in vitro cytocompatibility studies on graphene, the coating is likely to introduce some bias in short-term cultures. In a long-term culture or an in vivo implant, however, the coating will end up dissolving/degrading after a couple of weeks and this might reveal a toxicity hidden by the presence of coated proteins masking the graphene surface.

This is not the case in this study, because even with short-term cultures graphene is investigated both bare and coated with proteins. A second important novelty aspect of this work is the use of cultures of adult neurons on graphene, which is in contrast to previous studies reporting on cultures obtained from embryonic or new-born tissues. Aiming at testing materials for neuroprosthetic devices, cytocompatibility studies using adult neurons provide a more realistic model system since these prostheses are to be implanted in adult patients.

These results demonstrates that adult neurons can survive and grow neurites when cultured on bare (i.e. non-coated with peptides) graphene, confirming its great potential as a cytocompatible material for interfacing neurons with electronic devices. In a recent development, graphene transistor arrays have been successfully used to record action potentials from cardiomyocytes [Hess, et al., 2011, Cohen-Karni, et al., 2010].

Example 3: Coating Protocol

A solution of poly-D-lysine at 2 µg/cm$^2$ is prepared in Phosphate Buffer Saline (PBS). A drop of this poly-D-lysine solution, typically between 100 µL and 1 mL depending on the size of the implant, is deposited at the basis of the electrodes, so that the electrode tips are not immersed, and left for 45 minutes to incubate. The basis of the electrodes is then rinsed in PBS and a solution of laminine at 1 μg/cm² is applied also at the basis of the electrodes. The incubations steps are done in a humidified chamber (37° C., 5% CO2).

Examples 4: Electrodes

Electrodes were prepared as previously described in Djilas et al., 2011 and coated according to the above described process to provide coated devices.

Briefly, 3D electrode geometries and their corresponding half cross sections are as illustrated in FIGS. 19 (A) and (B). The dashed lines in the 3D representations mark geometry half cross sections. Each electrode half cross section is defined with five parameters (p1-p5) which represent the lengths of the segments.

Cavity wall inclination is 54.7° for both geometries. Active electrode segments (thick lines in the half cross sections) are separated by insulated segments (thin lines in the half cross sections).

Two implant models are described herein. They consist of a conductive plane in which there is a cavity. The stimulating electrode is at the bottom of the cavity, whereas the contra-electrode is a conductive plane surrounding the cavity. The two active electrode surfaces can be separated by insulating sidewalls inside the cavity. Both electrode structures are axially symmetric and can thus be defined by their half cross sections (FIGS. 19, (A) and (B).

The two models differ in the arrangement and the active and insulating surfaces inside the cavity. In one configuration, the stimulating electrode does not cover the entire cavity bottom; there is an insulating section between the stimulating electrode and the cavity sidewall. In configuration B, the stimulating electrode covers the entire cavity bottom and extends onto the lower part of the cavity wall. In both configurations, the contra-electrode extends from the top surface onto the sidewalls in the cavity.

The half cross sections can be defined using five parameters, p1-p5, which are the lengths of individual segments constituting the model geometries. Electrically active electrode surfaces are the thick segments, while the insulating surfaces are the thin segments.

For configuration A, these five parameters are:
(p1) stimulating electrode radius, (p2) distance from stimulating electrode edge to the cavity sidewall, (p3) the length of the insulating segment on the cavity sidewall, (p4) the length of the contra-electrode segment that extends onto the cavity sidewall and (p5) the length of the horizontal segment of the contra-electrode.

For configuration B, these parameters are: (p1) the length of the horizontal segment of the stimulating electrode, (p2) the length of the stimulating electrode segment that extends onto the cavity sidewall, (p3) distance from the stimulating electrode to the contra-electrode, (p4) the length of the contraelectrode segment extending onto the cavity sidewall and (p5) the length of the horizontal segment of the contra-electrode.

In configuration A, the stimulating electrode is at the bottom of the well (parameter p1) surrounded by an isolating layer (p2), while the returning grid is at the surface of the implant (p5), which can be extended on the descending well wall (parameter p4).

In configuration B, the stimulating electrode and the returning grid can both extend on the well wall with parameters p2 and p4, respectively.

The electrodes are micro fabricated using a classical silicon wet etching process which is why the inclination of the cavity sidewall was fixed to the etching angle (54.7°) for (1 0 0) silicon.

Finite-element models may be created using the Comsol Multiphysics Modeling and Simulation software package (Comsol AB). The physical model used in the simulations is the two-dimensional axially symmetric DC conductive media model, defined by the following relationships:

$J=\sigma E$,
$\nabla J=Q$,
$Q=-\nabla(\sigma \nabla V)$, where J is the current density vector, E is the electric field vector, σ is the electric conductivity of the media, Q is the electric charge and V is the electric potential.

Electrode geometries are optimized using MATLAB (The Mathworks) to find optimal model parameters that yield the best stimulation selectivity. Optimizations are performed under the additional constraints that the fabrication mask openings, corresponding to the electrically active electrode surfaces, must be at least 5 μm apart, and the depth of the cavity does not exceed 50 μm. Implant with optimized parameters corresponding to the well depth of 30 μm and the well diameter of 30 μm (measured at the electrode array common plane level) were fabricated.

Selectivity improves with increased cavity depth. With depths up to 20 μm (corresponding to the lower edge of the stimulation target zone), there is little difference between the two configurations A and B Electrode selectivity reaches its peak at the depth of 30 μm for both configurations. Configuration B yields better selectivity than configuration A for all stimulating electrode sizes.

The difference is most prominent for smaller stimulating electrode sizes, e.g. for p1=5 μm, there is approximately a threefold increase in selectivity when optimal geometry B is compared to optimal geometry A, and a tenfold increase when optimal geometry B is compared to the optimal planar electrode structure.

To eventually pack as many electrodes as possible in a limited space, it is of interest to have parameters p1 and p5 as small as possible.

This will result in having the minimal size of a single electrode and therefore also the minimal center to-center inter-electrode distance in an array.

Example 4-1: Finite-Element Models of Four Variations of a 25×25 Stimulating Electrode Array Inside a Retinal Prosthetic System Finite-element models of four variations of a 25×25 stimulating electrode array inside a retinal prosthetic system were prepared: (i) a planar array with a common counter electrode with the shape of a grid surrounding the stimulating electrodes, (ii) a planar electrode array with a distant counter electrode, (iii) a three-dimensional electrode array with a stimulation electrode surrounded by a grid again serving as a counter electrode; and (iv) a 3D electrode with a distant counter electrode. All were coated according to the present invention. The inter-electrode distance was kept at 100 μm and the well depth for the 3D models was 30 μm. All other model parameters were the same as described in (Djilas et al, 2011) or in WO2011135273 (A1) which methods and processes are incorporated herein by reference.

For simulation purposes an image of Abraham Lincoln was then cropped and down sampled into a square 25×25 image and its color palette reduced from 256 to 3 colors:

white, gray, and black (see FIGS. 13 (A) and (B)). This resulting image was then mapped into a finite-element models by assigning current densities to the stimulating electrodes that are proportional to the colors in the cropped image: zero for white, 1000 A/m² for gray and 2000 A/m² for black.

Example 4-2: Implant Fabrication

The implant templates used in this study were made of polyimide. Some of the implants were fabricated alternatively using boron doped diamond (BDD) or platinum electrodes for comparison purposes. A few other implants were left blank without electrodes.

The implants including BDD electrodes were fabricated as follows: silicon moulds were prepared using KOH wet etching: in order to achieve truncated pyramids, a specific design was needed, where a structure was added to compensate the etching speed of the 110 and 100 oriented crystalline plans. The process was stopped when the cavities of the silicon moulds were typically reaching 30 µm in height. A final mould is shown in FIG. 15.

FIG. 14 shows an example of Electrode modeling. This observation is confirmed by the panels showing the side views of stimulated planar electrodes on which there seems to be more crosstalk between two neighboring electrodes. Indeed, this crosstalk is much reduced with the 3D electrodes, and the pixels on the images generated with the 3D configurations present a higher resolution (Djilas et al, 2011).

A specific process allowing the selective growth of BDD electrodes onto the substrate was used as described elsewhere (Girard et al., 2009). This process consists of depositing seeds of nano-diamond (approximately 5 nm in diameter) over the substrate. Then an aluminum mask is sputtered over the substrate and patterned by photolithography. Finally the unprotected nano-diamond is etched away by reactive ion etching (RIE) under oxygen plasma and the aluminium mask removed by wet etching. A Microwave Plasma Enhanced Chemical Vapour Deposition (MPECVD) reactor is used to synthesize the boron-doped diamond in a gas mixture of methane ($CH_4$) and hydrogen ($H_2$) and trimethyl boron (TMB) using growth conditions as described elsewhere (Kiran et al., 2012, 12, 7669).

The thickness of the diamond layer obtained was approximately 300 nm and the doping level was in the order of $2.5 \times 10^{21}$ boron at·cm$^{-3}$.

In a particular embodiment, the thickness of the diamond layer obtained is comprised from less than 500 nm, preferably less than 300 nm and more preferably is comprised from 300 to 180 nm.

The doping level is from 0.01 to $100 \times 10^{21}$ boron at·cm$^{-3}$, preferably from 1 to $10 \times 10^{21}$ boron at·cm$^{-3}$ and more preferably is $2.5 \times 10^{21}$ boron at·cm$^{-3}$.

Polyimide (PI 2611) was then spin coated over the substrate so that a 10 µm-thick layer of polymer was obtained. The polyimide was then cured at 450° C. under nitrogen flow for 6 hours, and a 500 nm-thick aluminium film was sputtered. Finally AZ4562 (Clariant, Muttenz, Switzerland) thick photoresist is spin coated on the wafer to define the implant shape, after the development the wafer was placed in Chlorine RIE to etch the aluminium layer. The unmasked polymer was etched away by $O_2$ RIE in order to achieve the final shape of the implant. The wafer was immersed in hydrofluoric acid (HF) in order to etch the sacrificial oxide layer and release the individual implants. Finally the implants were rinsed in DI water and dried.

The process used to prepare the implant with platinum electrodes was similar. Here the step of BDD electrode deposition was replaced by a deposition of Pt electrodes sputtered over the substrate and patterned by standard photolithography. A third series of implants was prepared in the same way except that no electrodes were deposited on the implants at all.

Electron microscopy imaging was performed using a Field Emission Scanning Electron Microscope (SEM) ZEISS Supra-40, operating with an acceleration voltage of 2 kV. The implants were imaged by SEM after the implantation period. In order to perform SEM imaging, the retina/implant ensembles were fixed in paraformaldehyde, the retina was peeled off, and the implants were dehydrated in ethanol baths of increasing concentrations in water (50%, 70%, 90% and 100% ethanol).

Example 4-2: Surgical Procedure & In Vivo Imaging

Homozygous P23H rats (Lewin et al., 1998; Machida et al., 2000) were housed with a 12 h dark/light cycle with food and water available ad libitum. All Experiments were carried out in accordance with the European Community Council Directives (86/609/EEC) and with the ARVO (Association for Research in Vision and Ophthalmology) statement for the Use of animals in ophthalmic and visual Research. Animals were sacrificed by $CO_2$ sedation and cervical dislocation, and all efforts were made to minimize suffering.

The surgical procedure used to implant the prototypes was described in detail previously (Salzmann et al., 2006). Briefly, P23H blind rats were anesthetized by intraperitoneal injection with a 4:1 mixture of ketamine-xylazine (ketamine 100 mg kg$^{-1}$, xylazine 10 mg kg$^{-1}$) (Ketamine 500: Virbac, Carros, France; xylazine 2%: Rompun®, Bayer Pharma, Puteaux, France). A small radial sclerotomy (length 1.5 mm) was made behind the limbus with a slit knife. Viscoat® Intraocular viscoelastic Injection (Alcon Laboratories, Hünenberg, Switzerland) was injected with a 27 G canula into the subretinal space through the sclerotomy in order to obtain a localised retinal detachment. After inducing a retinal detachment, the implant was inserted into the subretinal space. Immediately after surgery, the correct position of the implant was controlled in vivo with indirect ophthalmoscopy (frost and lens).

In vivo imaging was performed one week after surgery and six weeks later, right before the sacrifice to observe the eye fundus by endoscopy. A MicronIII numerical endoscope (Phoenix Research Laboratories, Pleasanton, Calif.) was used for imaging the eye fundus, with the StreamPix V software with rat probe.

Example 4-3: Immunostaining, Confocal Imaging and Quantification

After 6 to 8 weeks, animals were sacrificed by $CO_2$ sedation and cervical elongation. The eyes were removed, put in phosphate buffer saline (PBS, 0.1 M, pH 7.4) and dissected to keep only the tissue fragment containing the implant. This fragment was fixed overnight at 4° C. in PBS containing paraformaldehyde (4% wt/vol) and then rinsed in PBS.

For immunolabelling, retina fragments were incubated in a blocking solution (PBS containing 10% bovine serum albumin (Sigma, St. Louis, Mo.), 1% Triton X-100 (Sigma), 0.5% Tween 20 (Sigma) and 0.1 g/L Thimerosal (Sigma)) for 1 h at room temperature (room temperature is from 22°

C. to 25° C., in particular 20° C.). Primary antibodies were incubated for 2 days at room temperature in the blocking solution (dilution 1:2). Polyclonal antibodies were directed against chicken GFAP (1:100, LSBio, Seattle, Wash.) and rabbit PKCα (C-20) (1:1000, Santa Cruz Biotechnology, Dallas, Tex.). Monoclonal antibody was directed against mouse Goα (1:200, Chemicon, Darmstadt, Germany). The fragments were rinsed and then incubated with secondary antibodies, goat anti-chicken IgG, goat anti-mouse IgG and goat anti-rabbit conjugated to Alexa™ 633, Alexa™ 594 and Alexa™ 488 respectively (1:500, Molecular Probes, Invitrogen, Eugene, Oreg.) for one day. Cell nuclei were revealed with 4',6-Diamidino-2-phenylindole (DAPI) which was added during the final incubation period. The implant/retina ensemble was then rinsed and mounted with Permanent Mounting medium (MMFrance) on a microscope slide to be visualized under an upright confocal microscope (Olympus, France).

The presence of bipolar cells within the wells of 3D-structured implants was quantified as the ratio of bipolar cells over the total number of cell nuclei per well for each material and was counted semi-automatically with Imaris software (Bitplane AG, Zurich, Switzerland).

Example 4-4: Statistical Analysis

The results from 3 polyimide implants, 5 diamond implants and 3 platinum implants, taking the values from 4 to 9 wells per implant for quantification were collected. All data are expressed as means±s.e.m. Gaussian distribution of raw data was tested with Shapiro-Wilk normality test. A one-way ANOVA was used for variance analysis, followed in case of significance by either a Bonferroni post-hoc test (Gaussian distribution) or a Dunns post-hoc test (no Gaussian distribution) to compare the means of each group. Differences were considered significant at $*p<0.05$, $p<0.01$ and $*p<0.001$.

Example 4-5: Diamond Electrodes on a Flexible Foil

The possibility to fabricate flexible substrates that adapt to the curvature of soft tissues such as the retina is essential. Synthesis techniques enabling the growth of diamond rely on high temperatures and microwave plasma techniques that are not compatible with most types of soft substrates.

It is one object of the present invention to provide a substrate that adapts to the curvature of soft tissues.

The solution we developed is based on a lift-off process for which a soft polymer deposited on top of a patterned diamond layer is used to provide support to the diamond layer. A soft polymer deposited on top of a patterned diamond layer supporting a diamond layer, is provided.

It is within the scope of the person skilled in the art to determine the softness or hardness of polymer and of devices according to the invention. For example, a high resolution nanoindenter or Depth-Sensing Indentation (DSI) technique may be used, to evaluate mechanical properties of materials at the nanoscale level, especially hardness.

This process is displayed on FIG. 15 (A) and the device is fabricated based on the mask shown in FIG. 15 (B).

In brief, this was made feasible from the selective growth of the diamond electrodes on a rigid sacrificial substrate (silicon mould on FIG. 15 C), on which is prepared the polyimide structure, which is released from the substrate at the end of the process. The approach enables large dimensions to be fabricated as visible on FIG. 15 D.

A process comprising a selective growth of a diamond electrode on a substrate, in particular a silicon mould, preparing a polyimide structure, optionally releasing said polyimide structure from the substrate.

Example 4-6: In Vivo Imaging

Soft polyimide implants with diamond and metal electrodes were inserted into the subretinal space of P23H rats (animal model of photoreceptor degeneration) for 6 to 8 weeks, to assess the tissue reaction. The correct implant insertion was controlled in vivo using a MicronIII numerical endoscope, see fundus images on 16. The presence of retinal blood vessels above the device confirmed the subretinal position of the implants. This examination also enabled us to visualize the resorbtion of the subretinal bleb generated to introduce the subretinal implant.

Example 4-7: Characterization of Diamond Implants

The original fabrication process enabled fabricating soft implants exhibiting several 3D wells either uncoated or coated with either diamond or Platinum. In the case of diamond the coating covers the whole area on the implant visible on the photograph FIGS. 17 B and E, including the walls and the bottom of the cavities, whereas in the case of platinum the metal coverage appears in light grey color in panels C and F. After 6 to 8 weeks of implantation, the surface of the implanted electrodes was observed by Scanning Electron Microscopy (SEM) in order to assess the physical stability of the implants. The results are shown in FIG. 17 for the three materials tested. On the polyimide implant (A, D), the surface of the material is similar to before implantation, with no visible defect. Note that the white trace visible on FIG. 17 A is due to charge accumulation on this insulating surface during SEM imaging. Similarly, the diamond films (B, E) showed no discontinuities and proper surface coverage, thus suggesting a good adhesion of diamond onto polyimide. Those diamond surfaces appeared very smooth as opposed to conventional polycrystalline BDD. This is because the way the implants are fabricated, the side of diamond that is actually exposed to the tissues is the smooth face that was originally in contact with the silicon surface.

Finally on the metallic implants (C, F), the light grey areas corresponding to platinum appear also free of significant defects and darker because of organic matter (remaining cells). Hence the surface of both diamond and platinum has not been damaged during the implantation period. For all these implants, some cells or tissue remain visible on the implants and are particularly concentrated inside the cavities on the enlarged views (D-F). To validate the presence of retinal neurons, particularly bipolar cells, we have investigated the nature of these remaining cells within the 3D structures by immunostaining and confocal imaging. The results are shown in the following section.

Example 4-8: Bipolar Cell Migration

To study the interface between a tissue and a prosthetic device, sections are commonly prepared with or without removing the device prior to sectioning. However, although this histological procedure could be performed in previous studies on polyimide prototypes (Salzman et al., 2006; Djilas et al., 2011), the presence of metallic as well as BDD electrodes makes this approach unrealistic without degrading the observed samples. In fact, according to the mechanical stiffness of some of the polyimide prototypes, the cryo-sections of the implants frequently induced the dissociation of the samples as previously illustrated (Djilas et al., 2011). Greater difficulties were anticipated with the presence of metal or diamond electrodes on the implants. Therefore, to preserve the biological samples, an innovative approach based on confocal microscopy was developed and enabling the direct observation of the tissue/implant interface. Retinal bipolar neurons and glial cells were immunolabelled as a wholemount preparation containing both the retina and the implant. The immunostaining protocol was adapted to preserve this interaction while allowing antibody diffusion within the retinal tissue over a 100 µm distance. FIG. 18 illustrates such confocal images of the tissue/implant interface for a diamond implant (A-B), along with the image processing for cell quantification (C-E).

Cell nuclei were labeled by the DAPI stain (blue) while glial cells and retinal bipolar neurons were immunolabelled by the GFAP antibody (grey) and the Goα and PKCα antibodies (green and red), respectively. The ×20 magnification view of the retina/implant wholemount (A) allows visualizing the presence of nuclei stain in all 25 cavities. The ×40 magnification images (panel B) allows a better observation of the morphology of bipolar cells filling the cavities. The vertical views (x-z axes) similar to vertical retinal sections showed retinal bipolar neurons in green filling the entire cavity up to the bottom. The horizontal views (x-y axes) confirmed that the bipolar neurons were present at high densities within each well regardless of the materials.

To further assess the material biocompatibility, the number of cell nuclei was quantified in the cavities (D) as well as the percentage of bipolar neurons versus all cell nuclei in each cavity (E). This quantification required to isolate all pixels in a single well, to define in this volume the spheres corresponding to the immunolabelling of bipolar cell nuclei and to count them (C). FIG. 18 illustrates these cell counts of all ON bipolar cells in the wells with different materials. These images provide evidence that the residual retina remains very plastic to mould itself into the 3D implant wells. Furthermore, the absence of a massive fibrotic inflammatory reaction but rather the presence of bipolar neurons in the wells suggests that the different materials according to the invention are not toxic to neurons.

Conclusion:

The results with our 3D prototypes inserted in the sub-retinal space of P23H rats showed that the retina shapes into the wells with bipolar cell neurons fully integrating the inside of the cavities. The present invention provides a physical confinement of the stimulus. These experiments also indicated an increased stability of the tissue/implant interface with 3D prototypes than with planar implants. As a consequence, stimulating bipolar cells in such a well would activate a retinal column independent from the neighboring retinal columns activated by the neighboring wells. Our three-dimensional design of the subretinal implants would therefore allow considering each electrode as an independent pixel.

Our results show the compatibility of diamond with flexible implant fabrication, the low tissue scarring in contact with diamond electrodes and the possibility to selectively stimulate neurons in the vicinity of each electrode independently from the neighboring electrodes. Our study clearly demonstrates that nanocrystalline diamond is safe for the retinal tissue and more generally for glial cells and neurones during chronic implantation.

The object of the present invention is therefore a major improvement as compared to those disclosed in prior art.

This study confirms the benefit of 3D-structured electrodes for the conception of retinal implants to tremendously improve the resolution of the stimulation. It also underlines the high interest diamond offers as an attractive electrode material for neuroprostheses, in particular flexible neuroprostheses.

REFERENCES

Adler, R. *Methods in Neurosciences* 1990, 2, 134.
Ariano P, Lo Giudice A, Marcantoni A, Vittone E, Carbone E, Lovisolo D (2009) A diamond-based biosensor for the recording of neuronal activity. Biosensors and Bioelectronics 24:2046.
Barres B A, Silverstein B E, Corey D P, Chun L L Y (1988) Immunological, Morphological, And Electrophysiological Variation Among Retinal Ganglion-Cells Purified By Panning Neuron 1:791-803.
Butterwick A, Huie P, Jones B W, Marc R E, Marmor M, Palanker D (2009) Effect of shape and coating of a subretinal prosthesis on its integration with the retina. Exp Eye Res 88:22-29.
Chang J C B G, Wheeler B C (2001) Modulation of network activity by patterning. Biosens Bioelectron 7.
Clark, P., D. Coles, M. Peckham, *Experimental Cell Research* 1997, 230, 275;
Cohen-Karni, T., Q. Qing, Q. Li, Y. Fang, C. M. Lieber, *Nano Letters* 2010, 10, 1098].
Dankerl, M., Moritz V. Hauf, Andreas Lippert, Lucas H. Hess, Stefan Birner, Ian D. Sharp, Ather Mahmood, Pierre Mallet, Jean-Yves Veuillen, Martin Stutzmann, Jose A. Garrido, "Graphene Solution-Gated Field-Effect Transistor Array for Sensing Applications Advanced Funtional Materials, 20 (2010) 3117-3124;
Djilas M, Oles C, Lorach H, Bendali A, Degardin J, Dubus E, Lissorgues-Bazin G, Rousseau L, Benosman R, Ieng S H, Joucla S, Yvert B, Bergonzo P, Sahel J, Picaud S (2011) Three-dimensional electrode arrays for retinal prostheses: modeling, geometry optimization and experimental validation. J Neural Eng 8:046020.
Dobelle W H, Mladejovsky M G, Girvin J P (1974) Artificial vision for the blind: electrical stimulation of visual cortex offers hope for a functional prosthesis. Science 183:440-444.
Fricke, R., P. D. Zentis, L. T. Rajappa, B. Hofmann, M. Banzet, A. Offenhäusser, S. H. Meffert, *Biomaterials* 2011, 32, 2070
Fuchs C, Forster V, Balse E, Sahel J-A, Picaud S, Tessier L-H (2005a) Retinal-Cell-Conditioned Medium Prevents TNF-alpha-Induced Apoptosis of Purified Ganglion Cells. Investigative Ophthalmology & Visual Science 46:2983.
Fuchs C, Forster V, Balse E, Sahel J A, Picaud S, Tessier L H (2005b) Retinal-cell-conditioned medium prevents TNF-alpha-induced apoptosis of purified ganglion cells. Invest Ophthalmol Vis Sci 46:2983-2991.
Girard H A, Perruchas S, Gesset C, Chaigneau M, Vieille L, Arnault J C, Bergonzo P, Boilot J P, Gacoin T, Electrostatic grafting of diamond nanoparticles: a versatile route to nanocrystalline diamond thin films, ACS Applied Materials and Interfaces 2009, 1, 2738
Grausova L B L, Kromka A, Potocky S, Vanecek M, Nesladek M, Lisa V. (2009) Nanodiamond as promising material for bone tissue engineering. J Nanosci Nanotechnol 9:3524-3534.

Gupta S, Dudipala A, Williams O A, Haenen K, Bohannan E (2008) Ex situ variable angle spectroscopic ellipsometry studies on chemical vapor deposited boron-doped diamond films: Layered structure and modeling aspects. Journal Of Applied Physics 104.

Hess, L. H. M. Jansen, V. Maybeck, M. V. Hauf, M. Seifert, M. Stutzmann, I. D. Sharp, A. Offenhäusser, J. A. Garrido, *Advanced Materials* 2011, 23, 5045.

Jung, D. R., R. Kapur, T. Adams, K. A. Giuliano, M. Mrksich, H. G. Craighead, D. L. Taylor, *Critical Reviews in Biotechnology* 2001, 21, 111.

Humayun M S, Dorn J D, Ahuja A K, Caspi A, Filley E, Dagnelie G, Salzmann J, Santos A, Duncan J, Dacruz L, Mohand-Said S, Eliott D, McMahon M J, Greenberg R J (2009) Preliminary 6 month results from the argus II epiretinal prosthesis feasibility study. Conf Proc IEEE Eng Med Biol Soc 1:4566-4568.

Khan, S., G. Newaz, *Journal Biomedical Materials Research Part. A* 2010, 93, 1209.

Kiran R, Rousseau L, Lissorgues G, Scorsone E, Bongrain A, Yvert B, Picaud S, Mailley P, Bergonzo P, Multichannel boron doped nanocrystalline diamond ultramicroelectrode arrays: design, fabrication and characterization, Sensors 2012, 12, 7669.

Lebedev M A, Nicolelis M A L (2006) Brain-machine interfaces: past, present and future. Trends in Neurosciences 29:536.

Lewin A S, Drenser K A, Hauswirth W W, Nishikawa S, Yasumura D, Flannery J G, LaVail M M (1998) Ribozyme rescue of photoreceptor cells in a transgenic rat model of autosomal dominant retinitis pigmentosa. Nat Med 4:967-971.

Li, N., X. Zhang, Q. Song, R. Su, Q. Zhang, T. Kong, L. Liu, G. Jin, M. Tang, G. Cheng, *Biomaterials* 2011, 32, 9374.

Li, X, W. Cai, J. An, S. Kim, J. Nah, D. Yang, R. Piner, A. Velamakanni, I. Jung, E. Tutuc, S. K. Banerjee, L. Colombo, R. S. Ruoff, *Science* 2009, 324, 1312.

Liu, B. F., J. Ma, Q. Y. Xu, F. Z. Cui, *Colloids and Surfaces B: Biointerfaces* 2006, 53, 175.

Lions M, Saada S, Mazellier J P, Andrieu F, Faynot O, Bergonzo P (2009) Ultra-thin nanocrystalline diamond films (<100 nm) with high electrical resistivity. Physica Status Solidi-Rapid Research Letters 3:205-207.

Machida S, Kondo M, Jamison J A, Khan N W, Kononen L T, Sugawara T, Bush R A, Sieving P A (2000) P23H rhodopsin transgenic rat: correlation of retinal function with histopathology. Invest Ophthalmol Vis Sci 41:3200-3209.

Maynard E M, Fernandez E, Normann R A (2000) A technique to prevent dural adhesions to chronically implanted microelectrode arrays. Journal of Neuroscience Methods 97:93.

Mrksich M, Dike L E, Tien J, Ingber D E, Whitesides G M (1997) Using microcontact printing to pattern the attachment of mammalian cells to self-assembled mono layers of alkanethiolates on transparent films of gold and silver. Experimental Cell Research 235:305-313.

Park, S. Y., J. Park, S. H. Sim, M. G. Sung, K. S. Kim, B. H. Hong, S. Hong, *Advanced Healthcare Materials* 2011, 23, 263.

Salzmann J, Linderholm O P, Guyomard J L, Paques M, Simonutti M, Lecchi M, Sommerhalder J, Dubus E, Pelizzone M, Bertrand D, Sahel J, Renaud P, Safran A B, Picaud S (2006) Subretinal electrode implantation in the P23H rat for chronic stimulations. In, pp 1183-1187.

Specht C G, Williams O A, Jackman R B, Schoepfer R (2004) Ordered growth of neurons on diamond. Biomaterials 25:4073.

Thalhammer A, Edgington R J, Cingolani L A, Schoepfer R, Jackman R B (2010) The use of nanodiamond monolayer coatings to promote the formation of functional neuronal networks. Biomaterials 31:2097-2104.

Watkins, T. A., B. Emery, S. Mulinyawe, B. A. Barres, *Neuron* 2008, 60, 555.

Yen, S., W. Hsu, Y. Chen, H. Su, Y. Chang, H. Chen, S. Yeh, T. Yew, *Biosensors Bioelectronics* 2011, 26, 4124.

Zhang, Y., S. F. Ali, E. Dervishi, Y. Xu, Z. Li, D. Casciano, A. S. Biris, *ACS Nano* 2010, 4, 3181.

Zrenner E, Bartz-Schmidt K U, Benav H, Besch D, Bruckmann A, Gabel V P, Gekeler F, Greppmaier U, Harscher A, Kibbel S, Koch J, Kusnyerik A, Peters T, Stingl K, Sachs H, Stett A, Szurman P, Wilhelm B, Wilke R (2011) Subretinal electronic chips allow blind patients to read letters and combine them to words. Proc Biol Sci 278: 1489-1497.

The invention claimed is:

1. A method for promoting growth or at least direct interfacing of adult neurons on an electrode without substantially promoting growth and direct interfacing of glial cells on at least part of said electrode, comprising:
   contacting tissue comprising adult neurons with an electrode comprising a first part formed from a first biocompatible chemically oxygen terminated or H-terminated carbon-based material and a second part formed from a second biocompatible chemically oxygen terminated or H-terminated carbon-based material, said first carbon-based material being bound to said second carbon-based material,
   wherein said first carbon-based material is selected from the group consisting of nanocrystalline diamond doped with boron, phosphorus or nitrogen to become a semiconductor, graphene, nanotubes, and nanotubes on diamond, said first carbon-based material has a surface that is substantially free of any peptide coating to promote growth or at least direct interfacing of adult neurons on said first part of said electrode without substantially promoting growth and direct interfacing of glial cells on said first part of said electrode, and said first carbon-based material has an electrical conductivity of at least about 0.01 S·cm$^{-1}$, and
   wherein said second carbon-based material is identical or different from said first carbon-based material, said second carbon-based material has a surface that includes a peptide coating, to promote growth and at least direct interfacing of adult glial cells on said second part of said electrode, and said second carbon-based material is selected from the group consisting of nanocrystalline diamond doped with boron, oxidized diamond, graphene, and nanotubes.

2. The method according to claim 1, wherein said tissue comprising adult neurons is selected from the group consisting of retina, thalamus, cortex, vestibular system, cochlea, brain stem, midbrain, colliculus, subthalamic nucleus, globus pallidus interna, zona incerta, pallidofugal fibers, periaqueductal gray, periventricular gray, internal capsule, ventral posterolateral nucleus and ventral posteromedial nucleus, subgenual cingulate gyrus, nucleus accumbens, ventral capsule/ventral striatum, inferior thalamic peduncle, lateral habenula vagus nerve, afferent nerves, spinal cord, large dorsal columns, and nerves controlling muscle activity.

3. The method according to claim 1, wherein:
said electrode is a penetrating electrode, or said electrode is positioned on a penetrating support,
said penetrating electrode or said electrode positioned on a penetrating support has a length from about 10 μm to about 1 to 2 cm and a diameter from 20 μm to about 500 μm.

4. The method according to claim 3, wherein, said penetrating electrode is one of a plurality of penetrating electrodes combined to form a penetrating electrode array, and said penetrating electrode array is fixed on a support to form an implant or a prosthesis.

5. The method according to claim 1, wherein said electrode is a penetrating electrode fixed to a prosthesis or an implant, and said first part constitutes a tip of said penetrating electrode and said second part constitutes an interfacing surface between the prosthesis or implant and the glial surface of any neuronal structure.

6. The method according to claim 5, wherein said penetrating electrode is one of a plurality of penetrating electrodes fixed to said prosthesis or said implant, as a penetrating electrode array, and said first part constitutes a tip of each of said plurality of penetrating electrodes and said second part constitutes interfacing surfaces of each of said plurality of penetrating electrodes between the prosthesis or implant and the glial surface of any neuronal structure.

7. The method according to claim 1, wherein:
said peptide coating of said second carbon-based material is formed from a peptide selected from the group consisting of poly-lysine, poly-ornithine, laminin and combinations thereof, and
said peptide coating having a thickness from about 0.5 μg/cm² to about 5 μg/cm².

8. An electrode comprising:
a first part formed from a first chemically oxygen terminated or H-terminated carbon-based material, said first carbon-based material being substantially free of any peptide coating to promote growth or at least direct interfacing of adult neurons, without substantially promoting growth and direct interfacing of glial cells on said first part of said electrode,
a second part formed from a second biocompatible chemically oxygen terminated or H-terminated carbon-based material, identical or different from said first carbon-based material, said second carbon-based material being bound to said first carbon-based material, said second carbon-based material having a peptide coating to promote the growth and at least the direct interfacing of adult glial cells on said second part of said electrode, and
wherein said first and second carbon-based material are independently selected from the group consisting of nanocrystalline diamond which is doped with boron, phosphorus or nitrogen to become a semiconductor, graphene, nanotubes, and nanotubes on diamond.

9. The electrode according to claim 8, wherein said electrode is a penetrating electrode.

10. The electrode according to claim 9, wherein:
said peptide coating is formed from a peptide selected from the group consisting of poly-lysine, poly-ornithine, and laminin,
said peptide coating has a thickness from about 0.5 μg/cm² to about 5 μg/cm², and
said electrode has a length from about 10 μm to about 1 to 2 cm and a diameter from 20 μm to about 500 μm.

11. The electrode according to claim 8, wherein said electrode is a penetrating electrode, and said first part constitutes a tip of said penetrating electrode and said second part constitutes an interfacing surface configured for positioning between a prosthesis or implant and a glial surface of any neuronal structure.

12. A process for preparing an electrode according to claim 8, comprising the following steps:
a) preparing a conductive biocompatible chemically oxygen terminated or H-terminated carbon-based material scaffold, said chemically oxygen terminated or H-terminated carbon-based material scaffold comprising a first part and a second part,
b) optionally oxidizing said first part of said chemically oxygen terminated or H-terminated carbon-based material scaffold to obtain an optionally oxidized first part of said chemically oxygen terminated or H-terminated carbon-based material scaffold, said optionally oxidized first part being a first carbon-based material,
c) optionally doping said second part of said chemically oxygen terminated or H-terminated carbon-based material scaffold with boron, phosphorus or nitrogen, to obtain an optionally doped second part of said chemically oxygen terminated or H-terminated carbon-based material scaffold,
d) coating said optionally doped second part of said chemically oxygen terminated or H-terminated carbon-based material scaffold with a peptide to obtain a second carbon-based material,
wherein said first carbon-based material is substantially free of any peptide coating, and
wherein said first carbon based material and said second carbon-based material constitute an electrode.

13. The method according to claim 12, wherein said peptide is selected from the group consisting of poly-lysine, poly-ornithine, and laminin.

14. The process according to claim 12, further comprising doping said first chemically oxygen terminated or H-terminated carbon-based material with boron, phosphorus or nitrogen.

15. The process according to claim 12, wherein said first chemically oxygen terminated or H-terminated carbon-based material is nanocrystalline diamond, polycrystalline diamond, or graphene.

16. The process according to claim 12, wherein said second chemically oxygen terminated or H-terminated carbon-based material is nanocrystalline diamond, polycrystalline diamond, or graphene.

17. The electrode according to claim 8, wherein said penetrating electrode has a needle shape.

18. A method of implementing an implant or a prosthesis liable to promote growth of adult neurons or at least direct interfacing of adult neurons and to stimulate said adult neurons, comprising contacting an electrode as defined in claim 14 with tissue comprising adult neurons.

19. The method according to claim 18, wherein said electrode has a form selected from the group consisting of:
(i) said electrode is one of a planar array of electrodes in contact with said tissue, said planar array having a common counter electrode with a shape of a grid surrounding a stimulating electrodes,
(ii) said electrode is one of a planar electrode array of electrodes in contact with said tissue, said planar electrode array having a distant counter electrode,
(iii) said electrode is a three-dimensional electrode, and
(iv) said electrode is a three-dimensional electrode and is combined with a distant counter electrode with an inter-electrode distance of 100 μm.

20. The method according to claim 18, wherein said neurons are retinal neurons and said implant is a retinal implant.

\* \* \* \* \*